(12) United States Patent
Clements

(10) Patent No.: US 11,434,261 B2
(45) Date of Patent: Sep. 6, 2022

(54) OPTIMIZED ZIKA VIRUS ENVELOPE GENE AND EXPRESSION THEREOF

(71) Applicant: Hawaii Biotech Inc., Honolulu, HI (US)

(72) Inventor: David E. Clements, Honolulu, HI (US)

(73) Assignee: Hawaii Biotech Inc., Honolulu, HI (US)

(*) Notice: Subject to any disclaimer, the term of this patent is extended or adjusted under 35 U.S.C. 154(b) by 217 days.

(21) Appl. No.: 16/320,983

(22) PCT Filed: Jul. 26, 2017

(86) PCT No.: PCT/US2017/044008
§ 371 (c)(1),
(2) Date: Jan. 25, 2019

(87) PCT Pub. No.: WO2018/022790
PCT Pub. Date: Feb. 1, 2018

(65) Prior Publication Data
US 2021/0332084 A1   Oct. 28, 2021

Related U.S. Application Data

(60) Provisional application No. 62/442,346, filed on Jan. 4, 2017, provisional application No. 62/410,572, filed on Oct. 20, 2016, provisional application No. 62/367,310, filed on Jul. 27, 2016.

(51) Int. Cl.
| | |
|---|---|
| *C07K 14/005* | (2006.01) |
| *A61P 31/14* | (2006.01) |
| *A61K 39/12* | (2006.01) |
| *A61K 39/39* | (2006.01) |
| *C12N 15/85* | (2006.01) |
| *A61K 39/00* | (2006.01) |

(52) U.S. Cl.
CPC ............ *C07K 14/005* (2013.01); *A61K 39/12* (2013.01); *A61K 39/39* (2013.01); *A61P 31/14* (2018.01); *C12N 15/85* (2013.01); *A61K 2039/55555* (2013.01); *A61K 2039/55566* (2013.01); *A61K 2039/55577* (2013.01); *C12N 2770/24122* (2013.01); *C12N 2770/24134* (2013.01); *C12N 2770/24152* (2013.01); *C12N 2770/24171* (2013.01)

(58) Field of Classification Search
None
See application file for complete search history.

(56) References Cited

U.S. PATENT DOCUMENTS

| | | | |
|---|---|---|---|
| 6,165,477 | A | 12/2000 | Ivy et al. |
| 7,838,006 | B2 | 11/2010 | Jirathitikal et al. |
| 9,267,114 | B2 | 2/2016 | Yamshchikov |
| 2003/0175304 | A1 | 9/2003 | Peters et al. |
| 2009/0226489 | A1 | 9/2009 | Jira et al. |
| 2012/0263754 | A1 | 10/2012 | Dubensky et al. |

FOREIGN PATENT DOCUMENTS

| | | |
|---|---|---|
| AU | 2007202304 A1 | 6/2007 |
| CN | 105749268 A | 7/2016 |
| EP | 2221368 A1 | 8/2010 |
| EP | 16162688.2 * | 3/2016 |
| WO | WO 2017/109222 A1 | 6/2017 |

OTHER PUBLICATIONS

Dai et al., Cell Host & Microbe, May 11, 2016, 19:696-704. (Year: 2016).*
Dai et al., "Structures of the Zika Virus Envelope Protein and its Complex with a Flavivirus Broadly Protective Antibody," *Cell Host & Microbe* (2016), 19:696-704, Elsevier Inc.

* cited by examiner

*Primary Examiner* — Stacy B Chen
(74) *Attorney, Agent, or Firm* — DLA Piper LLP (US)

(57) ABSTRACT

The present invention is directed to the expression and secretion the Zika virus envelope protein. Elements of the pre-membrane and envelope sequence have been modified to enhance the expression of the envelope protein as a secreted product in the culture medium of transformed insect cell lines. The expressed and purified product is suitable as a vaccine antigen.

7 Claims, 9 Drawing Sheets
Specification includes a Sequence Listing.

Pre-membrane and envelope sequence of Zika virus French Polynesia strain H/PF/2013 with translation

```
|-> prM
gcggaggucacuagacgugggagugcauacuauauguacuuggacagaaacgacgcuggg   60
 A  E  V  T  R  R  G  S  A  Y  Y  M  Y  L  D  R  N  D  A  G gaggccauaucuuuuccaaccacauuggggaugaauaaguguuauauacagaucauggau  120
 E  A  I  S  F  P  T  T  L  G  M  N  K  C  Y  I  Q  I  M  D cuuggacacaugugugaugccaccaugagcaugaaugcccuaugcuggaugagggggug  180
 L  G  H  M  C  D  A  T  M  S  Y  E  C  P  M  L  D  E  G  V gaaccagaugacgucgauuguuggugcaacacgacgucaacuuggguuguguacggaacc  240
 E  P  D  D  V  D  C  W  C  N  T  T  S  T  W  V  V  Y  G  T ugccaucacaaaaaggugaagcacggagaucuagaagagcugugacgcuccccucccau  300
 C  H  H  K  K  G  E  A  R  R  S  R  R  A  V  T  L  P  S  H uccacuaggaagcugcaaacgcggucgcaaaccugguuggaaucaagagaauacacaaag  360
 S  T  R  K  L  Q  T  R  S  Q  T  W  L  E  S  R  E  Y  T  K cacuugauuagagucgaaaauuggauauucaggaacccuggcuucgcguuagcagcagcu  420
 H  L  I  R  V  E  N  W  I  F  R  N  P  G  F  A  L  A  A  A Gccaucgcuuggcuuuugggaagcucaacgagccaaaaagucauauacuuggucaugaua  480
 A  I  A  W  L  L  G  S  S  T  S  Q  K  V  I  Y  L  V  M  I
                                        |-> E
cugcugauugccccggcauacagcaucaggugcauaggagucagcaauagggacuuugug  540
 L  L  I  A  P  A  Y  S  I  R  C  I  G  V  S  N  R  D  F  V gaagguaugucaggugggacuuggguugauguugucuuggaacauggagguugugucacc  600
 E  G  M  S  G  G  T  W  V  D  V  V  L  E  H  G  G  C  V  T guaauggcacaggacaaaccgacugucgacauagagcugguuacaacaacagucagcaac  660
 V  M  A  Q  D  K  P  T  V  D  I  E  L  V  T  T  T  V  S  N auggcggagguaagauccuacugcuaugaggcaucaauaucggacauggcuucggacagc  720
 M  A  E  V  R  S  Y  C  Y  E  A  S  I  S  D  M  A  S  D  S cgcugcccaacacaaggugaagccuaccuugacaagcaaucagacacucaauaugucugc  780
 R  C  P  T  Q  G  E  A  Y  L  D  K  Q  S  D  T  Q  Y  V  C aaaagaacguuaguggacagaggcuggggaaauggaugugacuuuuggcaagggagc    840
 K  R  T  L  V  D  R  G  W  G  N  G  C  G  L  F  G  K  G  S cuggugacaugcgcuaaguuugcaugcuccaagaaaaugaccgggaagagcauccagcca  900
 L  V  T  C  A  K  F  A  C  S  K  K  M  T  G  K  S  I  Q  P gagaaucuggaguaccggauaaugcugucaguucauggcucccagcacagugggaugauc  960
 E  N  L  E  Y  R  I  M  L  S  V  H  G  S  Q  H  S  G  M  I
```

FIGURE 1

```
guuaaugacacaggacaugaaacugaugagaauagagcgaagguugagauaacgcccaau    1020
 V  N  D  T  G  H  E  T  D  E  N  R  A  K  V  E  I  T  P  N ucaccaagagccgaagccacccuggggguuuuggaagccuaggacuugauugugaaccg      1080
 S  P  R  A  E  A  T  L  G  G  F  G  S  L  G  L  D  C  E  P aggacaggccuugacuuuucagauuuguauuacuugacuaugaauaacaagcacugguug    1140
 R  T  G  L  D  F  S  D  L  Y  Y  L  T  M  N  N  K  H  W  L guucaaggagugguuccacgacauuccauuaccuuggcacgcuggggcagacaccgga      1200
 V  H  K  E  W  F  H  D  I  P  L  P  W  H  A  G  A  D  T  G acuccacacuggaacaacaaagaagcacgguagaguucaaggacgcacaugccaaaagg     1260
 T  P  H  W  N  N  K  E  A  L  V  E  F  K  D  A  H  A  K  R caaacugucgugguucuagggagucaagaaggagcaguucacacggcccuugcuggagcu    1320
 Q  T  V  V  L  G  S  Q  E  G  A  V  H  T  A  L  A  G  A cuggaggcugagauggauggugcaaagggaaggcugccucuggccacuugaaaugucgc     1380
 L  E  A  E  M  D  G  A  K  G  R  L  S  S  G  H  L  K  C  R cugaaaauggauaaacuuagauugaagggcgugucauacuccuuguguaccgcagcguuc    1440
 L  K  M  D  K  L  R  L  K  G  V  S  Y  S  L  C  T  A  A  F acauucaccaagaucccggcugaaacacugcacgggacagucacaguggagguacaguac    1500
 T  F  T  K  I  P  A  E  T  L  H  G  T  V  T  V  E  V  Q  Y gcagggacagauggaccuugcaagguuccagcucagauggcgguggacaugcaaacucug    1560
 A  G  T  D  G  P  C  K  V  P  A  Q  M  A  V  D  M  Q  T  L accccaguugggagguugauaaccgcuaaccccguaaucacugaaagcacugagaacucu    1620
 T  P  V  G  R  L  I  T  A  N  P  V  I  T  E  S  T  E  N  S aagaugaugcuggaacuugauccaccauuugggacucuuacauugucauaggagucggg     1680
 K  M  M  L  E  L  D  P  P  F  G  D  S  Y  I  V  I  G  V  G gagaagaagaucacccaccacuggcacaggaguggcagcaccauuggaaaagcauuugaa    1740
 E  K  K  I  T  H  H  W  H  R  S  G  S  T  I  G  K  A  F  E gccacugugagaggugccaagagaauggcagucuugggagacacagccgggacuuugga    1800
 A  T  V  R  G  A  K  R  M  A  V  L  G  D  T  A  W  D  F  G ucaguuggaggcgcucucaacucauugggcaagggcauccaucaaauuuuuggagcagcu    1860
 S  V  G  G  A  L  N  S  L  G  K  G  I  H  Q  I  F  G  A  A uucaaaucauuguuuggaggaauguccugguucucacaaauucucauuggaacguugcug    1940
 F  K  S  L  F  G  G  M  S  W  F  S  Q  I  L  I  G  T  L  L auggguuggucugaacacaaagaauggaucuauuucccuuaugugcuuggccuuaggg     2000
 M  W  L  G  L  N  T  K  N  G  S  I  S  L  M  C  L  A  L  G ggaguguugaucuucuuauccacagcugucucugcug                            2017
 G  V  L  I  F  L  S  T  A  V  S  A
```

FIGURE 1 CONT'D

Codon optimized pre-membrane and envelope (80E) sequence of Zika virus

```
GCAGAAGTGACCCGCCGCGGCAGCGCATACTATATGTACCTCGATCGTAACGACGCGGGC
GAAGCTATCTCCTTCCCGACCACGCTGGGCATGAACAAGTGCTATATTCAGATTATGGAC
CTGGGCCATATGTGCGACGCGACCATGTCCTACGAATGTCCGATGCTGGACGAAGGAGTT
GAGCCTGATGACGTCGATTGCTGGTGCAATACCACTTCCACCTGGGTGGTGTACGGTACT
TGCCATCACAAAAGGGCGAAGCCCGCCGTTCCCGTCGCGCTGTCACTCTGCCAAGCCAC
AGCACACGCAAATTGCAGACGAGGAGTCAGACGTGGTTGGAGTCGCGCGAGTACACAAAG
CACCTGATTCGGGTGGAAAATTGGATCTTCCGGAATCCGGGCTTTGCTTTGGCGGCAGCC
GCTATTGCGTGGCTGCTCGGCAGTAGCACGTCGCAGAAAGTGATTTACCTGGTCATGATC
CTCCTCATCGCCCCCGCCTATTCGATCCGTTGCATTGGCGTCAGCAACCGCGATTTCGTG
GAGGGCATGAGCGGTGGAACCTGGGTCGACGTTGTGCTGGAACATGGCGGCTGCGTCACA
GTGATGGCTCAGGACAAGCCGACCGTGGACATCGAGTTGGTTACCACGACGGTTTCCAAC
ATGGCGGAGGTTCGCAGCTACTGCTACGAAGCCAGCATCAGCGATATGGCATCGGACAGC
CGGTGCCCGACCCAGGGAGAAGCATATCTCGACAAGCAGTCCGACACGCAATATGTCTGT
AAAAGGACGCTCGTTGACCGCGGCTGGGCAACGGCTGCGGCCTGTTTGGAAAAGGCTCC
CTGGTCACATGCGCGAAGTTTGCATGTTCGAAGAAGATGACGGGCAAAAGCATCCAACCA
GAGAATCTGGAATACCGGATCATGTTGTCCGTGCACGGCAGCCAGCATAGTGGCATGATT
GTGAACGACACCGGTCACGAAACCGACGAGAACCGCGCTAAAGTTGAGATCACCCCGAAC
AGTCCCCGGGCCGAGGCCACGCTGGGAGGCTTCGGATCGCTGGGTCTGGATTGCGAACCC
CGCACCGGACTGGATTTCTCGGATCTCTACTACCTGACGATGAACAATAAGCACTGGCTG
GTGCACAAAGAGTGGTTCCATGATATCCCATTGCCCTGGCATGCCGGTGCCGATACCGGA
ACACCCCACTGGAACAATAAGGAGGCCCTGGTCGAGTTTAAGGACGCGCACGCTAAGCGT
CAAACGGTGGTGGTGCTGGGATCCCAAGAGGGCGCCGTGCACACGGCCCTGGCCGGCGCG
CTGGAGGCCGAGATGGACGGTGCCAAGGGACGCTTGAGCTCCGGACACCTGAAATGCCGC
CTCAAGATGGACAAGCTGCGTCTGAAAGGAGTGTCCTACTCCCTCTGCACCGCCGCGTTC
ACCTTCACTAAGATTCCCGCCGAGACTTTGCACGGTACAGTGACCGTTGAGGTGCAGTAT
GCCGGAACCGATGGCCCTTGCAAAGTCCCGGCCCAAATGGCGGTGGATATGCAGACGCTG
ACGCCTGTGGGCCGGCTCATTACCGCAAACCCAGTCATCACGGAGAGTACCGAGAACTCG
AAGATGATGCTGGAGTTGGACCCCCGTTTGGCGACAGTTACATCGTGATCGGAGTGGGC
GAAAAGAAGATTACGCACCATTGGCACCGTAGCGGC
```

FIGURE 2

Expression of codon optimized ZIPFP-80E-CoOp in *Drosophila* S2 cells. Samples were run 10% SDS PAGE gel under non-reducing conditions and stained with Coomassie Blue.

Comparison of flavivirus secretion signals at the prM-E junction along with an optimized synthetic secretion signal for expression of the Zika virus envelope protein.

```
                            -1+1
            |--M Trans Mem--|  |-E N-term    SigP Score
Zika        QKVIYLVMILLIAPAYS  IRCIGV        0.231
West Nile   QRVVFVVLLLLVAPAYS  FNCLGM        0.321
TBE-CEEV    TRVAVLVVLLCLAPVYA  SRCTHL        0.396
Omsk        TRVVIVAALLCLAPAYA  SRCTHL        0.417
Kyasanur    TRFIVITVALCLAPTYA  TRCTHL        0.351
YFV         QRVVIALLVLAVGPAYS  AHCIGI        0.274
DENV-1      QKGIIFILLMLVTPSMA  MRCVGI        0.351
DENV-2      QRVLIFILLTAIAPSMT  MRCIGI        0.295
DENV-3      QKVVIFILLILVTPSMA  MRCVGV        0.363
DENV-4      QRTVFFVLMMLVAPSYG  MRCVGV        0.316
SyntheticZ  MRTIIALLLLLVSGAHG  IRCIGV        0.347
Synthetic+  MRTIIALLLLLVSGAHA  SRCVGV        0.703
```

```
M   R   T   I   I   A   L   L   L   L   V   S   G   A   H   A   S   R   C   V   G   V
ATGCGCACCATCATTGCCCTGCTCTTGCTGCTCGTGAGCGGTGCCCACGCCAGCCGTTGCGTGGGTGTG
```

FIGURE 4

Alignment of flavivirus envelope proteins at the 80E junction

```
                                                           80E
                                                            |
ZIKV-H/PF/13  LITANPVITESTENSKMMLELDPPFGDSYIVIGVGEKKITHHWHRSGSTIGKAFEAT 414
DENV_1_       LITANPIVTDKE--KPVNIEAEPPFGESYIVIGAGEKALKLSWFKKGSSIGKMFEAT 405
DENV_2_       LITVNPIVTEKD--SPVNIEAEPPFGDSYIIIGVEPGQLKLNWFKKGSSIGQMFETT 405
DENV_3_       LITANPVVTKKE--EPVNIEAEPPFGESNIVIGIGDNALKINWYKKGSSIGKMFEAT 403
DENV_4_       IISSTPFAENTN--SVTNIELEPPFGDSYIVIGVGESALTLHWFRKGSSIGKMFEST 405
WNV_NY99      LVTVNPFVSVATANAKVLIELEPPFGDSYIVVGRGEQQINHHWHKSGSSIGKAFTTT 411
JEV_SA14      LVTVNPFVATSSANSKVLVEMEPPFGDSYIVVGRGDKQINHHWHKAGSTLGKAFSTT 410
YFV_          LVTVNPIASTND--DEVLIEVNPPFGDSYIIVGTGDSRLTYQWHKEGSSIGKLFTQT 403
              ::: .*.         :*  :****:* *::* :.      *.: **::*: *  *

ZIKV-H/PF/13  VRGAKRMAVLGDTAWDFGSVGG 436
DENV_1        ARGARRMAILGDTAWDFGSIGG 426
DENV_2        MRGAKRMAILGDTAWDFGSLGG 426
DENV_3        ARGARRMAILGDTAWDFGSVGG 424
DENV_4        YRGAKRMAILGETAWDFGSVGG 426
WNV_NY99      LKGAQRLAALGDTAWDFGSVGG 432
JEV_SA14      LKGAQRLAALGDTAWDFGSIGG 422
YFV_          MKGAERLAVMGDAAWDFSSAGG 424
              :**.*:* :*::****.* **
                                ****
```

FIGURE 5

ELISA results from mice serum following two (A) or three (B) doses of ZIKFP-80E-CoOp formulated with multiple adjuvants.

PRNT results from mice serum following two (A) or three (B) doses of ZIKFP-80E-CoOp formulated with multiple adjuvants.

HBV-008-M-001 Immungenicty Study Post Dose 2

FIGURE 7A

HBV-008-M-001 Immungenicty Study Post Dose 3

FIGURE 7B

Expression of ZIPFP-80E-WT, ZIKFP-80E-CoOp and ZIKFP-OpE-436 in Drosophila S2 cells. Samples were run 10% SDS PAGE gel under non-reducing conditions and stained with Coomassie Blue.

SEQUENCE LISTING

<160> NUMBER OF SEQ ID NOS: 29

<210> SEQ ID NO 1
<211> LENGTH: 1716
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Codon Optimized Zika prM-80E

<400> SEQUENCE: 1

```
gcagaagtga cccgccgcgg cagcgcatac tatatgtacc tcgatcgtaa cgacgcgggc     60
gaagctatct ccttcccgac cacgctgggc atgaacaagt gctatattca gattatggac    120
ctgggccata tgtgcgacgc gaccatgtcc tacgaatgtc cgatgctgga cgaaggagtt    180
gagcctgatg acgtcgattg ctggtgcaat accacttcca cctgggtggt gtacggtact    240
tgccatcaca aaaagggcga agcccgccgt tcccgtcgcg ctgtcactct gccaagccac    300
agcacacgca aattgcagac gaggagtcag acgtggttgg agtcgcgcga gtacacaaag    360
cacctgattc gggtggaaaa ttggatcttc cggaatccgg gctttgcttt ggcggcagcc    420
gctattgcgt ggctgctcgg cagtagcacg tcgcagaaag tgatttacct ggtcatgatc    480
ctcctcatcg cccccgccta ttcgatccgt tgcattggcg tcagcaaccg cgatttcgtg    540
gagggcatga gcggtggaac ctgggtcgac gttgtgctgg aacatggcgg ctgcgtcaca    600
gtgatggctc aggacaagcc gaccgtggac atcgagttgg ttaccacgac ggtttccaac    660
atggcggagg ttcgcagcta ctgctacgaa gccagcatca gcgatatggc atcggacagc    720
cggtgcccga cccagggaga agcatatctc gacaagcagt ccgacacgca atatgtctgt    780
aaaaggacgc tcgttgaccg cggctggggc aacggctgcg gcctgtttgg aaaaggctcc    840
ctggtcacat gcgcgaagtt tgcatgttcg aagaagatga cgggcaaaag catccaacca    900
gagaatctgg aataccggat catgttgtcc gtgcacggca gccagcatag tggcatgatt    960
gtgaacgaca ccggtcacga aaccgacgag aaccgcgcta aagttgagat caccccgaac   1020
agtccccggg ccgaggccac gctgggaggc ttcggatcgc tgggtctgga ttgcgaaccc   1080
cgcaccggac tggatttctc ggatctctac tacctgacga tgaacaataa gcactggctg   1140
gtgcacaaag agtggttcca tgatatccca ttgccctggc atgccggtgc cgataccgga   1200
acaccccact ggaacaataa ggaggccctg gtcgagttta aggacgcgca cgctaagcgt   1260
caaacggtgg tggtgctggg atcccaagag ggcgccgtgc acacggccct ggccggcgcg   1320
ctggaggccg agatggacgg tgccaaggga cgcttgagct ccggacacct gaaatgccgc   1380
ctcaagatgg acaagctgcg tctgaaagga gtgtcctact ccctctgcac cgccgcgttc   1440
accttcacta agattcccgc cgagactttg cacggtacag tgaccgttga ggtgcagtat   1500
gccggaaccg atggcccttg caaagtcccg gcccaaatgg cggtggatat gcagacgctg   1560
acgcctgtgg gccggctcat taccgcaaac ccagtcatca cggagagtac cgagaactcg   1620
aagatgatgc tggagttgga ccccccgttt ggcgacagtt acatcgtgat cggagtgggc   1680
```

```
gaaaagaaga ttacgcacca ttggcaccgt agcggc                              1716
```

<210> SEQ ID NO 2
<211> LENGTH: 1716
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Codon optimized nucleotide sequence for Zika
      prM-80E with synthetic E secretion signal

<400> SEQUENCE: 2

```
gcagaagtga cccgccgcgg cagcgcatac tatatgtacc tcgatcgtaa cgacgcgggc    60
gaagctatct ccttcccgac cacgctgggc atgaacaagt gctatattca gattatggac   120
ctgggccata tgtgcgacgc gaccatgtcc tacgaatgtc cgatgctgga cgaaggagtt   180
gagcctgatg acgtcgattg ctggtgcaat accacttcca cctgggtggt gtacggtact   240
tgccatcaca aaagggcga agcccgccgt tcccgtcgcg ctgtcactct gccaagccac    300
agcacacgca aattgcagac gaggagtcag acgtggttgg agtcgcgcga gtacacaaag   360
cacctgattc gggtggaaaa ttggatcttc cggaatccgg gctttgcttt ggcggcagcc   420
gctattgcgt ggctgctcgg cagtagcacg tcgatgcgca ccatcattgc cctgctcttg   480
ctgctcgtga gcggtgccca cgccagccgt tgcgtgggcg tcagcaaccg cgatttcgtg   540
gagggcatga gcgtggaac ctgggtcgac gttgtgctgg aacatggcgg ctgcgtcaca   600
gtgatggctc aggacaagcc gaccgtggac atcgagttgg ttaccacgac ggtttccaac   660
atggcgagg ttcgcagcta ctgctacgaa gccagcatca gcgatatggc atcggacagc   720
cggtgcccga cccagggaga agcatatctc gacaagcagt ccgacacgca atatgtctgt   780
aaaaggacgc tcgttgaccg cggctggggc aacggctgcg gcctgtttgg aaaaggctcc   840
ctggtcacat gcgcgaagtt tgcatgttcg aagaagatga cgggcaaaag catccaacca   900
gagaatctgg aataccggat catgttgtcc gtgcacggca gcagcatag tggcatgatt   960
gtgaacgaca ccgtcacga aaccgacgag aaccgcgcta agttgagat caccccgaac  1020
agtcccgggc cgaggccac gctgggaggc ttcggatcgc tgggtctgga ttgcgaaccc  1080
cgcaccggac tggatttctc ggatctctac tacctgacga tgaacaataa gcactggctg  1140
gtgcacaaag agtggttcca tgatatccca ttgccctggc atgccggtgc cgataccgga  1200
acccccact ggaacaataa ggaggccctg gtcgagttta aggacgcgca cgctaagcgt  1260
caaacggtgg tggtgctggg atcccaagag ggcgccgtgc acacggccct ggccggcgcg  1320
ctggaggccg agatggacgg tgccaaggga cgcttgagct ccggacacct gaaatgccgc  1380
ctcaagatgg acaagctgcg tctgaaagga gtgtcctact ccctctgcac cgccgcgttc  1440
accttcacta agattcccgc cgagactttg cacggtacag tgaccgttga ggtgcagtat  1500
gccggaaccg atgcccttg caaagtcccg gcccaaatgg cggtggatat gcagacgctg  1560
acgcctgtgg gccggctcat taccgcaaac ccagtcatca cggagagtac cgagaactcg  1620
aagatgatgc tggagttgga ccccccgttt ggcgacagtt acatcgtgat cggagtgggc  1680
gaaaagaaga ttacgcacca ttggcaccgt agcggc                            1716
```

<210> SEQ ID NO 3
<211> LENGTH: 1812
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Codon optimized nucleotide sequence for Zika
prM-E-436

<400> SEQUENCE: 3

```
gcagaagtga cccgccgcgg cagcgcatac tatatgtacc tcgatcgtaa cgacgcgggc     60
gaagctatct ccttcccgac cacgctgggc atgaacaagt gctatattca gattatggac    120
ctgggccata tgtgcgacgc gaccatgtcc tacgaatgtc cgatgctgga cgaaggagtt    180
gagcctgatg acgtcgattg ctggtgcaat accacttcca cctgggtggt gtacggtact    240
tgccatcaca aaaagggcga agcccgccgt tcccgtcgcg ctgtcactct gccaagccac    300
agcacacgca aattgcagac gaggagtcag acgtggttgg agtcgcgcga gtacacaaag    360
cacctgattc gggtggaaaa ttggatcttc cggaatccgg gctttgcttt ggcggcagcc    420
gctattgcgt ggctgctcgg cagtagcacg tcgcagaaag tgatttacct ggtcatgatc    480
ctcctcatcg cccccgccta ttcgatccgt tgcattggcg tcagcaaccg cgatttcgtg    540
gagggcatga gcggtggaac ctgggtcgac gttgtgctgg aacatggcgg ctgcgtcaca    600
gtgatggctc aggacaagcc gaccgtggac atcgagttgg ttaccacgac ggtttccaac    660
atggcggagg ttcgcagcta ctgctacgaa gccagcatca gcgatatggc atcggacagc    720
cggtgcccga cccagggaga agcatatctc gacaagcagt ccgacacgca atatgtctgt    780
aaaaggacgc tcgttgaccg cggctggggc aacggctgcg gcctgtttgg aaaaggctcc    840
ctggtcacat gcgcgaagtt tgcatgttcg aagaagatga cgggcaaaag catccaacca    900
gagaatctgg aataccggat catgttgtcc gtgcacggca gccagcatag tggcatgatt    960
gtgaacgaca ccggtcacga aaccgacgag aaccgcgcta aagttgagat cacccccgaac   1020 agtccccggg ccgaggccac gctgggaggc ttcggatcgc tgggtctgga ttgcgaaccc   1080
cgcaccggac tggatttctc ggatctctac tacctgacga tgaacaataa gcactggctg   1140
gtgcacaaag agtggttcca tgatatccca ttgccctggc atgccggtgc cgataccgga   1200
acaccccact ggaacaataa ggaggccctg gtcgagttta aggacgcgca cgctaagcgt   1260
caaacggtgg tggtgctggg atcccaagag ggcgccgtgc acacggccct ggccggcgcg   1320
ctggaggccg agatggacgg tgccaaggga cgcttgagct ccggacacct gaaatgccgc   1380
ctcaagatgg acaagctgcg tctgaaagga gtgtcctact ccctctgcac cgccgcgttc   1440
accttcacta agattcccgc cgagactttg cacggtacag tgaccgttga ggtgcagtat   1500
gccggaaccg atggcccttg caaagtcccg gcccaaatgg cggtggatat gcagacgctg   1560
acgcctgtgg gccggctcat taccgcaaac ccagtcatca cggagagtac cgagaactcg   1620
aagatgatgc tggagttgga ccccccgttt ggcgacagtt acatcgtgat cggagtgggc   1680
gaaaagaaga ttacgcacca ttggcaccgt agcggcagca ccatcggcaa ggccttcgag   1740
gccaccgtgc gcggcgccaa gcgcatggcc gtgctgggcg acaccgcctg ggacttcggc   1800
tccgtgggcg gc                                                         1812
```

<210> SEQ ID NO 4
<211> LENGTH: 1812
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Codon optimized nucleotide sequence for Zika
prM-E-436 with synthetic E secretion signal

<400> SEQUENCE: 4

```
gcagaagtga cccgccgcgg cagcgcatac tatatgtacc tcgatcgtaa cgacgcgggc     60
gaagctatct ccttcccgac cacgctgggc atgaacaagt gctatattca gattatggac    120
ctgggccata tgtgcgacgc gaccatgtcc tacgaatgtc cgatgctgga cgaaggagtt    180
gagcctgatg acgtcgattg ctggtgcaat accacttcca cctgggtggt gtacggtact    240
tgccatcaca aaaagggcga agcccgccgt tcccgtcgcg ctgtcactct gccaagccac    300
agcacacgca aattgcagac gaggagtcag acgtggttgg agtcgcgcga gtacacaaag    360
cacctgattc gggtggaaaa ttggatcttc cggaatccgg gctttgcttt ggcggcagcc    420
gctattgcgt ggctgctcgg cagtagcacg tcgatgcgca ccatcattgc cctgctcttg    480
ctgctcgtga gcggtgccca cgccagccgt tgcgtgggcg tcagcaaccg cgatttcgtg    540
gagggcatga gcggtggaac ctgggtcgac gttgtgctgg aacatggcgg ctgcgtcaca    600
gtgatggctc aggacaagcc gaccgtggac atcgagttgg ttaccacgac ggtttccaac    660
atggcggagg ttcgcagcta ctgctacgaa gccagcatca gcgatatggc atcggacagc    720
cggtgcccga cccagggaga agcatatctc gacaagcagt ccgacacgca atatgtctgt    780
aaaaggacgc tcgttgaccg cggctggggc aacggctgcg gcctgtttgg aaaaggctcc    840
ctggtcacat gcgcgaagtt tgcatgttcg aagaagatga cgggcaaaag catccaacca    900
gagaatctgg aataccggat catgttgtcc gtgcacggca gccagcatag tggcatgatt    960
gtgaacgaca ccggtcacga aaccgacgag aaccgcgcta aagttgagat caccccgaac   1020
agtccccggg ccgaggccac gctgggaggc ttcggatcgc tgggtctgga ttgcgaaccc   1080
cgcaccggac tggatttctc ggatctctac tacctgacga tgaacaataa gcactggctg   1140
gtgcacaaag agtggttcca tgatatccca ttgccctggc atgccggtgc cgataccgga   1200
acaccccact ggaacaataa ggaggccctg gtcgagttta aggacgcgca cgctaagcgt   1260
caaacggtgg tggtgctggg atcccaagag ggcgccgtgc acacggccct ggccggcgcg   1320
ctggaggccg agatggacgg tgccaaggga cgcttgagct ccggacacct gaaatgccgc   1380
ctcaagatgg acaagctgcg tctgaaagga gtgtcctact ccctctgcac cgccgcgttc   1440
accttcacta agattcccgc cgagactttg cacggtacag tgaccgttga ggtgcagtat   1500
gccggaaccg atggcccttg caaagtcccg gcccaaatgg cggtggatat gcagacgctg   1560
acgcctgtgg gccggctcat taccgcaaac ccagtcatca cggagagtac cgagaactcg   1620
aagatgatgc tggagttgga cccccgtttt ggcgacagtt acatcgtgat cggagtgggc   1680
gaaaagaaga ttacgcacca ttggcaccgt agcggcagca ccatcggcaa ggccttcgag   1740
gccaccgtgc gcggcgccaa gcgcatggcc gtgctgggcg acaccgcctg ggacttcggc   1800
tccgtgggcg gc                                                       1812
```

<210> SEQ ID NO 5
<211> LENGTH: 2016
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: French Polynesia prM-E nucleotide sequence

<400> SEQUENCE: 5

```
gcggaggtca ctagacgtgg gagtgcatac tatatgtact tggacagaaa cgacgctggg      60
gaggccatat cttttccaac cacattgggg atgaataagt gttatataca gatcatggat     120
cttggacaca tgtgtgatgc caccatgagc tatgaatgcc ctatgctgga tgagggggtg     180
gaaccagatg acgtcgattg ttggtgcaac acgacgtcaa cttgggttgt gtacggaacc     240
tgccatcaca aaaaggtga agcacggaga tctagaagag ctgtgacgct cccctcccat      300
tccactagga agctgcaaac gcggtcgcaa acctggttgg aatcaagaga atacacaaag     360
cacttgatta gagtcgaaaa ttggatattc aggaaccctg gcttcgcgtt agcagcagct     420
gccatcgctt ggcttttggg aagctcaacg agccaaaaag tcatatactt ggtcatgata     480
ctgctgattg ccccggcata cagcatcagg tgcataggag tcagcaatag ggactttgtg     540
gaaggtatgt caggtgggac ttgggttgat gttgtcttgg aacatggagg ttgtgtcacc     600
gtaatggcac aggacaaacc gactgtcgac atagagctgg ttacaacaac agtcagcaac     660
atggcggagg taagatccta ctgctatgag gcatcaatat cggacatggc ttcggacagc     720
cgctgcccaa cacaaggtga agcctacctt gacaagcaat cagacactca atatgtctgc     780
aaaagaacgt tagtggacag aggctgggga atggatgtg acttttttgg caaagggagc      840
ctggtgacat gcgctaagtt tgcatgctcc aagaaaatga ccgggaagag catccagcca     900
gagaatctgg agtaccggat aatgctgtca gttcatggct cccagcacag tgggatgatc     960
gttaatgaca caggacatga aactgatgag aatagagcga aggttgagat aacgcccaat    1020
tcaccaagag ccgaagccac cctgggggggt tttggaagcc taggacttga ttgtgaaccg    1080
aggacaggcc ttgacttttc agatttgtat tacttgacta tgaataacaa gcactggttg    1140
gttcacaagg agtggttcca cgacattcca ttaccttggc acgctgggggc agacaccgga    1200
actccacact ggaacaacaa agaagcactg gtagagttca aggacgcaca tgccaaaagg    1260
caaactgtcg tggttctagg gagtcaagaa ggagcagttc acacggcccct tgctggagct    1320
ctggaggctg agatggatgg tgcaaaggga aggctgtcct ctggccactt gaaatgtcgc    1380
ctgaaaatgg ataaacttag attgaagggc gtgtcatact ccttgtgtac cgcagcgttc    1440
acattcacca agatcccggc tgaaacactg cacgggacag tcacagtgga ggtacagtac    1500
gcagggacag atgaccttg caaggttcca gctcagatgg cggtggacat gcaaactctg    1560
accccagttg ggaggttgat aaccgctaac cccgtaatca ctgaaagcac tgagaactct    1620
aagatgatgc tggaacttga tccaccattt ggggactctt acattgtcat aggagtcggg    1680
gagaagaaga tcacccacca ctggcacagg agtggcagca ccattggaaa agcatttgaa    1740
gccactgtga gaggtgccaa gagaatggca gtcttgggag acacagcctg ggactttgga    1800
tcagttggag gcgctctcaa ctcattgggc aagggcatcc atcaaatttt tggagcagct    1860
ttcaaatcat tgtttggagg aatgtcctgg ttctcacaaa ttctcattgg aacgttgctg    1920
atgtggttgg gtctgaacac aaagaatgga tctatttccc ttatgtgctt ggccttaggg    1980
ggagtgttga tcttcttatc cacagctgtc tctgct                              2016
```

<210> SEQ ID NO 6
<211> LENGTH: 672
<212> TYPE: PRT
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: French Polynesia prM-E amino acid sequence

<400> SEQUENCE: 6

```
Ala Glu Val Thr Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Val Val
            180                 185                 190

Leu Glu His Gly Gly Cys Val Thr Val Met Ala Gln Asp Lys Pro Thr
        195                 200                 205

Val Asp Ile Glu Leu Val Thr Thr Thr Val Ser Asn Met Ala Glu Val
    210                 215                 220

Arg Ser Tyr Cys Tyr Glu Ala Ser Ile Ser Asp Met Ala Ser Asp Ser
225                 230                 235                 240

Arg Cys Pro Thr Gln Gly Glu Ala Tyr Leu Asp Lys Gln Ser Asp Thr
                245                 250                 255

Gln Tyr Val Cys Lys Arg Thr Leu Val Asp Arg Gly Trp Gly Asn Gly
            260                 265                 270

Cys Gly Leu Phe Gly Lys Gly Ser Leu Val Thr Cys Ala Lys Phe Ala
        275                 280                 285

Cys Ser Lys Lys Met Thr Gly Lys Ser Ile Gln Pro Glu Asn Leu Glu
    290                 295                 300

Tyr Arg Ile Met Leu Ser Val His Gly Ser Gln His Ser Gly Met Ile
305                 310                 315                 320

Val Asn Asp Thr Gly His Glu Thr Asp Glu Asn Arg Ala Lys Val Glu
                325                 330                 335

Ile Thr Pro Asn Ser Pro Arg Ala Glu Ala Thr Leu Gly Gly Phe Gly
            340                 345                 350

Ser Leu Gly Leu Asp Cys Glu Pro Arg Thr Gly Leu Asp Phe Ser Asp
        355                 360                 365

Leu Tyr Tyr Leu Thr Met Asn Asn Lys His Trp Leu Val His Lys Glu
    370                 375                 380

Trp Phe His Asp Ile Pro Leu Pro Trp His Ala Gly Ala Asp Thr Gly
385                 390                 395                 400
```

```
Thr Pro His Trp Asn Asn Lys Glu Ala Leu Val Glu Phe Lys Asp Ala
            405                 410                 415
His Ala Lys Arg Gln Thr Val Val Leu Gly Ser Gln Glu Gly Ala
            420                 425                 430
Val His Thr Ala Leu Ala Gly Ala Leu Glu Ala Glu Met Asp Gly Ala
            435                 440                 445
Lys Gly Arg Leu Ser Ser Gly His Leu Lys Cys Arg Leu Lys Met Asp
        450                 455                 460
Lys Leu Arg Leu Lys Gly Val Ser Tyr Ser Leu Cys Thr Ala Ala Phe
465                 470                 475                 480
Thr Phe Thr Lys Ile Pro Ala Glu Thr Leu His Gly Thr Val Thr Val
                485                 490                 495
Glu Val Gln Tyr Ala Gly Thr Asp Gly Pro Cys Lys Val Pro Ala Gln
            500                 505                 510
Met Ala Val Asp Met Gln Thr Leu Thr Pro Val Gly Arg Leu Ile Thr
            515                 520                 525
Ala Asn Pro Val Ile Thr Glu Ser Thr Glu Asn Ser Lys Met Met Leu
        530                 535                 540
Glu Leu Asp Pro Pro Phe Gly Asp Ser Tyr Ile Val Ile Gly Val Gly
545                 550                 555                 560
Glu Lys Lys Ile Thr His His Trp His Arg Ser Gly Ser Thr Ile Gly
                565                 570                 575
Lys Ala Phe Glu Ala Thr Val Arg Gly Ala Lys Arg Met Ala Val Leu
            580                 585                 590
Gly Asp Thr Ala Trp Asp Phe Gly Ser Val Gly Gly Ala Leu Asn Ser
            595                 600                 605
Leu Gly Lys Gly Ile His Gln Ile Phe Gly Ala Ala Phe Lys Ser Leu
        610                 615                 620
Phe Gly Gly Met Ser Trp Phe Ser Gln Ile Leu Ile Gly Thr Leu Leu
625                 630                 635                 640
Met Trp Leu Gly Leu Asn Thr Lys Asn Gly Ser Ile Ser Leu Met Cys
                645                 650                 655
Leu Ala Leu Gly Gly Val Leu Ile Phe Leu Ser Thr Ala Val Ser Ala
            660                 665                 670

<210> SEQ ID NO 7
<211> LENGTH: 725
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pHH202 expression vector cassette sequence

<400> SEQUENCE: 7
ggtaccgttg caggacagga tgtggtgccc gatgtgacta gctctttgct gcaggccgtc      60
ctatcctctg gttccgataa gagacccaga actccggccc ccaccgccc accgccaccc     120 ccatacatat gtggtacgca agtaagagtg cctgcgcatg ccccatgtgc cccaccaaga    180
gttttgcatc ccatacaagt ccccaaagtg agaaccgaa ccaattcttc gcgggcagaa     240
caaaagcttc tgcacacgtc tccactcgaa tttggagccg gcggcgtgt gcaaaagagg     300 tgaatcgaac gaaagacccg tgtgtaaagc cgcgtttcca aaatgtataa aaccgagagc    360
atctggccaa tgtgcatcag ttgtggtcag cagcaaaatc aagtgaatca tctcagtgca    420
```

```
actaaagggg gaatctagaa acaacatgaa gaccattatc gccctgtcgt acatcttttg    480
cctggtgttc gctagctcta gctagaggct cgaggcccct cgaaggatcc agacatgata    540
agatacattg atgagtttgg acaaaccaca actagaatgc agtgaaaaaa atgctttatt    600
tgtgaaattt gtgatgctat tgctttattt gtaaccatta taagctgcaa taaacaagtt    660
aacaacaaca attgcattca ttttatgttt caggttcagg gggaggtgtg ggaggttttt    720
taaag                                                                 725
```

<210> SEQ ID NO 8
<211> LENGTH: 23
<212> TYPE: PRT
<213> ORGANISM: Artificial Sequence
<220> FEATURE:
<223> OTHER INFORMATION: Synthetic

<400> SEQUENCE: 8

Gln Lys Val Ile Tyr Leu Val Met Ile Leu Leu Ile Ala Pro Ala Tyr
1               5                   10                  15

Ser Ile Arg Cys Ile Gly Val
            20

<210> SEQ ID NO 9
<211> LENGTH: 23
<212> TYPE: PRT
<213> ORGANISM: Artificial Sequence
<220> FEATURE:
<223> OTHER INFORMATION: Synthetic

<400> SEQUENCE: 9

Gln Arg Val Val Phe Val Val Leu Leu Leu Val Ala Pro Ala Tyr
1               5                   10                  15

Ser Phe Asn Cys Leu Gly Met
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic

<400> SEQUENCE: 10

Thr Arg Val Ala Val Leu Val Val Leu Leu Cys Leu Ala Pro Val Tyr
1               5                   10                  15

Ala Ser Arg Cys Thr His Leu
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Thr Arg Val Val Ile Val Ala Ala Leu Leu Cys Leu Ala Pro Ala Tyr
1               5                   10                  15

Ala Ser Arg Cys Thr His Leu
            20

<210> SEQ ID NO 12
<211> LENGTH: 23

<212> TYPE: PRT
<213> ORGANISM: Artificial Sequence
<220> FEATURE:
<223> OTHER INFORMATION: Synthetic

<400> SEQUENCE: 12

Thr Arg Phe Ile Val Ile Thr Val Ala Leu Cys Leu Ala Pro Thr Tyr
1               5                   10                  15

Ala Thr Arg Cys Thr His Leu
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic

<400> SEQUENCE: 13

Gln Arg Val Val Ile Ala Leu Leu Val Leu Ala Val Gly Pro Ala Tyr
1               5                   10                  15

Ser Ala His Cys Ile Gly Ile
            20

<210> SEQ ID NO 14
<211> LENGTH: 23
<212> TYPE: PRT
<213> ORGANISM: Artificial Sequence
<220> FEATURE:
<223> OTHER INFORMATION: Synthetic

<400> SEQUENCE: 14

Gln Lys Gly Ile Ile Phe Ile Leu Leu Met Leu Val Thr Pro Ser Met
1               5                   10                  15

Ala Met Arg Cys Val Gly Ile
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic

<400> SEQUENCE: 15

Gln Arg Val Leu Ile Phe Ile Leu Leu Thr Ala Ile Ala Pro Ser Met
1               5                   10                  15

Thr Met Arg Cys Ile Gly Ile
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic

<400> SEQUENCE: 16

Gln Lys Val Val Ile Phe Ile Leu Leu Ile Leu Val Thr Pro Ser Met
1               5                   10                  15

Ala Met Arg Cys Val Gly Val
            20

<210> SEQ ID NO 17

-continued

```
<211> LENGTH: 23
<212> TYPE: PRT
<213> ORGANISM: Artificial Sequence
<220> FEATURE:
<223> OTHER INFORMATION: Synthetic

<400> SEQUENCE: 17

Gln Arg Thr Val Phe Phe Val Leu Met Met Leu Val Ala Pro Ser Tyr
1               5                   10                  15

Gly Met Arg Cys Val Gly Val
            20

<210> SEQ ID NO 18
<211> LENGTH: 23
<212> TYPE: PRT
<213> ORGANISM: Artificial Sequence
<220> FEATURE:
<223> OTHER INFORMATION: Synthetic

<400> SEQUENCE: 18

Met Arg Thr Ile Ile Ala Leu Leu Leu Leu Val Ser Gly Ala His
1               5                   10                  15

Gly Ile Arg Cys Ile Gly Val
            20

<210> SEQ ID NO 19
<211> LENGTH: 23
<212> TYPE: PRT
<213> ORGANISM: Artificial Sequence
<220> FEATURE:
<223> OTHER INFORMATION: Synthetic

<400> SEQUENCE: 19

Met Arg Thr Ile Ile Ala Leu Leu Leu Leu Val Ser Gly Ala His
1               5                   10                  15

Ala Ser Arg Cys Val Gly Val
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic

<400> SEQUENCE: 20

Met Arg Thr Ile Ile Ala Leu Leu Leu Leu Val Ser Gly Ala His
1               5                   10                  15

Ala Ser Arg Cys Val Gly Val
            20

<210> SEQ ID NO 21
<211> LENGTH: 69
<212> TYPE: DNA
<213> ORGANISM: Artificial Sequence
<220> FEATURE:
<223> OTHER INFORMATION: Synthetic

<400> SEQUENCE: 21
atgcgcacca tcattgccct gctcttgctg ctcgtgagcg gtgcccacgc cagccgttgc    60
gtgggtgtg                                                            69

<210> SEQ ID NO 22
<211> LENGTH: 79
```

<212> TYPE: PRT
<213> ORGANISM: Artificial Sequence
<220> FEATURE:
<223> OTHER INFORMATION: Synthetic

<400> SEQUENCE: 22

Leu Ile Thr Ala Asn Pro Val Ile Thr Glu Ser Thr Glu Asn Ser Lys
1               5                   10                  15

Met Met Leu Glu Leu Asp Pro Pro Phe Gly Asp Ser Tyr Ile Val Ile
                20                  25                  30

Gly Val Gly Glu Lys Lys Ile Thr His His Trp His Arg Ser Gly Ser
            35                  40                  45

Thr Ile Gly Lys Ala Phe Glu Ala Thr Val Arg Gly Ala Lys Arg Met
        50                  55                  60

Ala Val Leu Gly Asp Thr Ala Trp Asp Phe Gly Ser Val Gly Gly
65                  70                  75

<210> SEQ ID NO 23
<211> LENGTH: 77
<212> TYPE: PRT
<213> ORGANISM: Artificial Sequence
<220> FEATURE:
<223> OTHER INFORMATION: Synthetic

<400> SEQUENCE: 23

Leu Ile Thr Ala Asn Pro Ile Val Thr Asp Lys Glu Lys Pro Val Asn
1               5                   10                  15

Ile Glu Ala Glu Pro Pro Phe Gly Glu Ser Tyr Ile Val Ile Gly Ala
                20                  25                  30

Gly Glu Lys Ala Leu Lys Leu Ser Trp Phe Lys Lys Gly Ser Ser Ile
            35                  40                  45

Gly Lys Met Phe Glu Ala Thr Ala Arg Gly Ala Arg Arg Met Ala Ile
        50                  55                  60

Leu Gly Asp Thr Ala Trp Asp Phe Gly Ser Ile Gly Gly
65                  70                  75

<210> SEQ ID NO 24
<211> LENGTH: 77
<212> TYPE: PRT
<213> ORGANISM: Artificial Sequence
<220> FEATURE:
<223> OTHER INFORMATION: Synthetic

<400> SEQUENCE: 24

Leu Ile Thr Val Asn Pro Ile Val Thr Glu Lys Asp Ser Pro Val Asn
1               5                   10                  15

Ile Glu Ala Glu Pro Pro Phe Gly Asp Ser Tyr Ile Ile Ile Gly Val
                20                  25                  30

Glu Pro Gly Gln Leu Lys Leu Asn Trp Phe Lys Lys Gly Ser Ser Ile
            35                  40                  45

Gly Gln Met Phe Glu Thr Thr Met Arg Gly Ala Lys Arg Met Ala Ile
        50                  55                  60

Leu Gly Asp Thr Ala Trp Asp Phe Gly Ser Leu Gly Gly
65                  70                  75

<210> SEQ ID NO 25
<211> LENGTH: 77
<212> TYPE: PRT
<213> ORGANISM: Artificial Sequence
<220> FEATURE:
<223> OTHER INFORMATION: Synthetic

<400> SEQUENCE: 25

Leu Ile Thr Ala Asn Pro Val Val Thr Lys Lys Glu Glu Pro Val Asn
1               5                   10                  15

Ile Glu Ala Glu Pro Pro Phe Gly Glu Ser Asn Ile Val Ile Gly Ile
            20                  25                  30

Gly Asp Asn Ala Leu Lys Ile Asn Trp Tyr Lys Lys Gly Ser Ser Ile
        35                  40                  45

Gly Lys Met Phe Glu Ala Thr Ala Arg Gly Ala Arg Met Ala Ile
50                  55                  60

Leu Gly Asp Thr Ala Trp Asp Phe Gly Ser Val Gly Gly
65                  70                  75

<210> SEQ ID NO 26
<211> LENGTH: 77
<212> TYPE: PRT
<213> ORGANISM: Artificial Sequence
<220> FEATURE:
<223> OTHER INFORMATION: Synthetic

<400> SEQUENCE: 26

Ile Ile Ser Ser Thr Pro Phe Ala Glu Asn Thr Asn Ser Val Thr Asn
1               5                   10                  15

Ile Glu Leu Glu Pro Pro Phe Gly Asp Ser Tyr Ile Val Ile Gly Val
            20                  25                  30

Gly Glu Ser Ala Leu Thr Leu His Trp Phe Arg Lys Gly Ser Ser Ile
        35                  40                  45

Gly Lys Met Phe Glu Ser Thr Tyr Arg Gly Ala Lys Arg Met Ala Ile
50                  55                  60

Leu Gly Glu Thr Ala Trp Asp Phe Gly Ser Val Gly Gly
65                  70                  75

<210> SEQ ID NO 27
<211> LENGTH: 79
<212> TYPE: PRT
<213> ORGANISM: Artificial Sequence
<220> FEATURE:
<223> OTHER INFORMATION: Synthetic

<400> SEQUENCE: 27

Leu Val Thr Val Asn Pro Phe Val Ser Val Ala Thr Ala Asn Ala Lys
1               5                   10                  15

Val Leu Ile Glu Leu Glu Pro Pro Phe Gly Asp Ser Tyr Ile Val Val
            20                  25                  30

Gly Arg Gly Glu Gln Gln Ile Asn His His Trp His Lys Ser Gly Ser
        35                  40                  45

Ser Ile Gly Lys Ala Phe Thr Thr Thr Leu Lys Gly Ala Gln Arg Leu
    50                  55                  60

Ala Ala Leu Gly Asp Thr Ala Trp Asp Phe Gly Ser Val Gly Gly
65                  70                  75

<210> SEQ ID NO 28
<211> LENGTH: 79
<212> TYPE: PRT
<213> ORGANISM: Artificial Sequence
<220> FEATURE:
<223> OTHER INFORMATION: Synthetic

<400> SEQUENCE: 28

Leu Val Thr Val Asn Pro Phe Val Ala Thr Ser Ser Ala Asn Ser Lys

```
                1               5                       10                      15
Val Leu Val Glu Met Glu Pro Pro Phe Gly Asp Ser Tyr Ile Val Val
                    20                      25                      30

Gly Arg Gly Asp Lys Gln Ile Asn His His Trp His Lys Ala Gly Ser
            35                      40                      45

Thr Leu Gly Lys Ala Phe Ser Thr Thr Leu Lys Gly Ala Gln Arg Leu
        50                      55                      60

Ala Ala Leu Gly Asp Thr Ala Trp Asp Phe Gly Ser Ile Gly Gly
65                      70                      75

<210> SEQ ID NO 29
<211> LENGTH: 77
<212> TYPE: PRT
<213> ORGANISM: Artificial Sequence
<220> FEATURE:
<223> OTHER INFORMATION: Synthetic

<400> SEQUENCE: 29

Leu Val Thr Val Asn Pro Ile Ala Ser Thr Asn Asp Asp Glu Val Leu
1               5                       10                      15

Ile Glu Val Asn Pro Pro Phe Gly Asp Ser Tyr Ile Ile Val Gly Thr
                    20                      25                      30

Gly Asp Ser Arg Leu Thr Tyr Gln Trp His Lys Glu Gly Ser Ser Ile
            35                      40                      45

Gly Lys Leu Phe Thr Gln Thr Met Lys Gly Ala Glu Arg Leu Ala Val
        50                      55                      60

Met Gly Asp Ala Ala Trp Asp Phe Ser Ser Ala Gly Gly
65                      70                      75
```

OPTIMIZED ZIKA VIRUS ENVELOPE GENE AND EXPRESSION THEREOF

CROSS-REFERENCE TO RELATED APPLICATIONS

This application is a 35 USC § 371 National Stage application of International Application No. PCT/US2017/044008 filed Jul. 26, 2017, now pending; which claims the benefit under 35 USC § 119(e) to U.S. Application Ser. No. 62/442,346 filed Jan. 4, 2017, U.S. Application Ser. No. 62/410,572 filed Oct. 20, 2016 and U.S. Application Ser. No. 62/367,310 filed Jul. 27, 2016, all now expired. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, name HBI1130_3WO_Sequence_Listing.txt was created on Jul. 25, 2017, and is 58 kb. The file can be assessed using Microsoft Word on a computer that uses Windows OS.

FIELD OF THE INVENTION

The invention relates generally to the design of optimized Zika virus envelope genes and expression thereof and more specifically to Zika virus vaccines.

BACKGROUND OF THE INVENTION

Zika virus (ZIKV) is a mosquito transmitted flavivirus whose recent spread through the Americas has caused the WHO to declare Zika a public health emergency of international concern (WHO 12 Feb. 2016; PAHO 14 Feb. 2016). Transmitted primarily by *Aedes* mosquitoes, infection with the positive strand RNA virus can lead to mild, dengue like symptoms: fever and rash sometimes associated with conjunctivitis, arthralgia or myalgia. Originally isolated in 1947 from a rhesus macaque during a yellow fever surveillance study in Uganda, ZIKV had caused sporadic outbreaks of acute, but mild disease in Africa, Asia and the Pacific Islands (Dick et al, 1952). During an intensive ZIKV outbreak in 2007 on Yap Island, 18% had clinical illness while 82% of those infected with ZIKV were asymptomatic (Duffy et al, 2009). ZIKV arrived in the Western hemisphere, Easter Island and Chile in 2014 (Tognarelli et al, 2014), then appeared in Brazil in early 2015 and since has spread to 33 countries and territories in the Caribbean, Central and South America and Mexico (PAHO 2 Apr. 2016). In addition to transmission by mosquitoes, there are reports of ZIKV being sexually transmitted. The first indication that ZIKV may also cause more severe neurological symptoms was the report of a 20-fold increase in the incidence of Guillain-Barré syndrome (GBS) during a 2013/2014 outbreak in French Polynesia (Oehler et al, 2014). A similar increase in GBS has been observed in the Americas coincident with the spread of ZIKV (WHO 2 Apr. 2016). In Bahia, Brazil, 26 of 42 GBS patients had historical symptoms consistent with ZIKV infection (PAHO 14 Feb. 2016; Schuller-Faccini et al, 2015). El Salvador and Colombia have reported a 3-fold increase in the incidence of GBS; 12 of 22 patients had febrile rash 7 to 15 days prior to onset (Schuller-Faccini et al, 2015; WHO 14 Feb. 2016). Honduras, Venezuela and Suriname also have reported an increase in GBS incidence; GBS cases have been reported during the ZIKV outbreak in Puerto Rico, Martinique, Panama, French Guiana, and Haiti (WHO 2 Apr. 2016). During the large and ongoing ZIKV pandemic in Brazil, there has been an increase in reports of infants born with microcephaly; up to 6480 suspected microcephaly cases have been reported in Brazil (PAHO 14 Feb. 2016; WHO 2 Apr. 2016). Given the association of GBS, microcephaly, and other birth defects with ZIKV infection, the development of a safe and effective vaccine for ZIKV is of paramount importance.

There is currently no approved vaccine for ZIKV. Multiple vaccine candidates have been discussed; all are in preclinical development (WHO 2 Apr. 2016). There have been at least 18 active vaccine research efforts identified by the WHO using the gamut of vaccine technologies including inactivated Zika virus, live attenuated viruses, viral vectors expressing ZIKV antigens, DNA vaccines, RNA vaccines, peptide vaccines, VLP vaccines and recombinant protein vaccines. It has been suggested that DNA vaccine candidates being developed by the Vaccine Research Center at NIH and Innovio Pharmaceuticals, Inc. may be able to start Phase 1 clinical testing this year. The target population for a ZIKV vaccine may include women of child bearing age and pregnant women. The risks of any replicating or genetic vaccine vector in this population would be significant. Therefore, a non-replicating, recombinant subunit protein is an attractive approach for a ZIKV vaccine as vaccines based on purified recombinant proteins provide for an improved safety profile. The key to success with the recombinant subunit approach for vaccines is the ability to efficiently produce high quality proteins that result in immune responses equivalent to, or better than, traditional live or inactivated virus approaches.

The choice of a recombinant protein expression system to employ is dependent on the desired application. The system of choice must meet key criteria such as proper folding and processing, consistency, and productivity (cost effectiveness) of the desired protein product (Schmidt, *Appl. Microbiol. Biotechnol.* (2004) 65:363-372). Insect cell-based expression systems have the potential to meet capacity requirements based on ease of culture, higher tolerance to osmolality and by-product concentrations during large scale culture, and generally higher expression levels (Ikonomou et al., *Appl. Microbiol Biotechnol.* (2003) 62:1-20). Recently, the use of expression systems based on insect cells has become more common. These systems provide most of the characteristics desired of eukaryotic systems, but have added benefits such as lower cost of goods. Insect cell systems are either based on infection of host cells with insect virus vectors (e.g., baculovirus) or on the generation of stable cell lines by integration of expression plasmids into the genome of the host cells.

The baculovirus expression system (BES) has emerged as the primary insect cell culture system utilized for recombinant protein expression. This system is based on the use of vectors derived from the insect viruses known as baculovirus. These vectors are used to generate recombinant viruses that encode the desired protein product. The recombinant viruses are used to infect host insect cells that then express the desired recombinant proteins. While there are advantages to this system in regards to ease of cloning and "time to product", there are also several disadvantages. The primary challenge in the use of BES is that it is based on the viral infection of the host cells. This results in cellular lysis and cell death 72-96 hrs post infection (Farrell et al., *Biotech. Biogen.* (1998) 60:656-663; Deo and Park, *Bio-* technol. Appl. Biochem. (2006) 43:129-135). As a result, during the late stages of infection the processing machinery of the insect cells is compromised to the extent that the processing of the desired product is also compromised. This limits the time that the cells can produce product and possibly more importantly leads to altered forms of the product being produced. Furthermore, the lysis of cells releases cellular enzymes that can also affect the quality of the desired product.

The use of stably transformed insect cells for the expression of recombinant proteins is an alternative to the use of BES. Expression systems based on stably transformed insect cell lines are non-lytic and provide for steady long term production of secreted products that require proper folding and post translational modifications. The secretion of the product into the culture medium provides a cleaner starting material for the purification process and allows for the final protein product to be purified with basic methods. This leads to products that are of higher quality (Kirkpatrick and Shatzman in *Gene Expression Systems: Using Nature for the Art of Expression* (1999) pp 289-330).

The *Drosophila melanogaster* cell expression system ("*Drosophila* expression system") is an established heterologous protein expression system based on the use of expression vectors containing *Drosophila* promoters and *Drosophila* S2 cells ("S2 cells") (Schneider, *Embryol. Exp. Morph.* (1972) 27:353-365). S2 cells are transformed with these vectors in order to establish stable cell lines expressing proteins corresponding to the heterologous sequences introduced into the vector (Johansen, H. et al., *Genes Dev.* (1989) 3:882-889; Ivey-Hoyle, M., *Curr. Opin. Biotechnol.* (1991) 2:704-707; Culp, J. S., et al., *Biotechnology* (NY) (1991) 9:173-177; U.S. Pat. Nos. 5,550,043; 5,681,713; 5,705,359; 6,046,025). This insect cell expression system has been shown to successfully produce a number of proteins from different sources. Examples of proteins that have been successfully expressed in the *Drosophila* S2 cell system include HIV gp120 (Culp, J. S., et al., *Biotechnology* (NY) (1991) 9:173-177; Ivey-Hoyle, M., *Curr. Opin. Biotechnol.* (1991) 2:704-707), human dopamine β-hydrolase (Bin et al., *Biochem. J.* (1996) 313:57-64), human vascular cell adhesion protein (Bernard et al., *Cytotechnol.* (1994) 15:139-144). In each of these examples, expression levels were greater than other expression systems that had been previously utilized.

In addition to high levels of expression, the *Drosophila* expression system has been shown to be able to express heterologous proteins that maintain native-like biological function (Bin et al., *Biochem. J.* (1996) 313:57-64), (Incardona and Rosenberry, *Mol. Biol. Cell.* (1996) 7:595-611). More recent examples have shown by means of X-ray crystallography studies that this expression system is capable of producing molecules with native-like structure (Modis et al., *Proc. Natl. Acad. Sci. USA* (2003) 100:6986-6991), (Modis et al., *Nature* (2004) 427:313-319), (Xu et al., *Acta. Crystallogr. D Biol. Crystallogr* (2005) 61:942-950). Two other recent publications have also demonstrated the ability of the *Drosophila* expression system to produce high quality products. In the first report, Schmetzer et al. (*J. Immun.* (2005) 174: 942-952) compares baculovirus-expressed EpCAM protein to *Drosophila*-expressed EpCAM protein for protein folding and native conformation. Specifically, BES-expressed EpCAM and *Drosophila*-expressed EpCAM were compared to denatured *Drosophila*-expressed EpCAM. It was determined that the BES-expressed EpCAM was in a partial folded state relative to the non-denatured and denatured *Drosophila*-expressed EpCAM protein. This indicates that the BES-expressed protein is in an incompletely folded state. The *Drosophila*-expressed EpCAM protein, on the other hand, adopted a more completely folded state. The authors of this paper considered the *Drosophila*-expressed protein to be in the "natural" state while the baculovirus-expressed protein was not. In the second report, Gardsvoll et al. (*Prot. Exp. Purif.* (2004) 34:284-295) demonstrate that the expression of the urokinase-type plasminogen activator receptor (uPAR) in S2 cells results in a more homogeneous product in regards to glycosylation (5 N-linked sites) than uPAR expressed in CHO cells.

The development of a recombinant subunit vaccine for ZIKV requires the selection of appropriate gene sequences from the ZIKV genome that encode proteins that are the target of neutralizing antibodies. Like other members of the flavivirus family, the envelope glycoprotein of ZIKV is the primary target of neutralizing antibodies. In addition to selection of an appropriate ZIKV gene sequence, efforts to optimize the expression of the selected gene sequences are also desirable to enhance the ability to effectively express the selected sequences such that the resultant products are soluble, stable and conformationally relevant.

While there are examples of flavivirus envelope gene sequences being expressed, there are no clear examples of optimizing the expression of these gene sequences as most examples are on the use of naturally occurring sequences of the parent viruses. Various means exist to optimize expression. However, each selected sequence requires several rounds of experimentation to determine which methods or combination of methods will result in the most effective expression in a given expression system while maintaining the appropriate native, or biologically relevant characteristics, which have the immunogenic potential to induce a neutralizing antibody response in the case of the ZIKV envelope gene sequence.

Problems are often encountered with virus envelope sequences that require maintenance of appropriate native or biologically relevant characteristic which can hamper optimal expression. These problems include non-optimal truncations that define the amino-terminus and the carboxy-terminus of the expressed product, poor or ineffective post translation processing, poor matching of the native codon usage with the codon usage of the selected expression system's host cells.

The efficiency of heterologous protein expression in eukaryotic systems is dependent on many factors, such as promoter and associated regulatory elements, transcription initiation sequences, and poly-adenylation signals. As the expression vectors used in a typical system are optimized for the given host cell utilized, the optimization of the gene sequence of interest is often of great importance to ensure optimal express of the desired protein product. This is typically done by adaptation of the codon usage of the gene sequence to the typical codon usage of the host cells. While the gene sequence is altered through codon optimization the amino acid sequence of the encoded protein in not modified through the optimization process (Gustafsson et al, 2004). Basic codon usage optimization involves substituting rare codons in the target gene sequence to ones used more frequently by the host cells. Alternatively, the entire gene sequence can be altered to be in line with the codon usage of the host cells used to express the desired product. With the current efficiency of de novo gene synthesis, the later approach has become the preferred method of codon optimization. As the expression of heterologous proteins is an important part of the biotechnology industry, methods such as codon optimization are often useful in improving expression levels.

Most proteins that are secreted from cells contain an N-terminal signal sequence that directs the protein into the cell's secretion pathway. Optimization of internal secretion signal or signal peptide sequence that interact with the endoplasmic membrane to initiate the secretion process has the potential to increase the efficiency of processing and hence and increase in protein expression. The eukaryotic signal sequence has been divided into three structural regions, basic, hydrophobic, and polar, starting from the N-terminus and proceeding to the C-terminus respectively (von Heijne, 1986 and Bendtsen et al 2004). Over the years numerous secretion signals have been identified and used to direct the secretion of recombinant proteins. Although many different signal sequences have been used and shown to be functional, few studies have been reported that define optimal sequences for a given cell type. The general characteristics and rules related to the three structural regions are well established, as detailed by von Heijne (1986) and by Bendtsen et al (2004), however, little comparative experimental data exist as to what constitutes an optimal secretion signal in a given expression system or a given heterologous protein being expressed. Most published reports deal with the characterization and optimization of gram positive bacterial or yeast secretion signals (Le Loir et al, 2005 and Hofmann and Schultz, 1991). One report that describes the optimization of the IL-2 secretion signal clearly demonstrates the benefits of optimization (Zhang et al, 2005).

Many eukaryotic proteins are modified by N-linked glycosylation (asparagine-linked). The of number sites and the efficiency of glycosylation by the enzyme oligosaccharyl-transferase can vary for each protein expressed can vary based on a number of factors. This can influence its expression and function. N-Linked glycosylation usually occurs at the Asn residues in the Asn-X-Ser/Thr motif, where X is any amino acid accept for Pro. However, many Asn-X-Ser/Thr sequences are not glycosylated or are glycosylated inefficiently (Mellquist et al, 1998). Inefficient glycosylation at one or more Asn-X-Ser/Thr sequences in a protein results in the production of heterogeneous glycoprotein products. The work of Mellquist et al has revealed that the amino acid at the Y position (amino acid residue immediately following the Ser or THr residue) is an important determinant of core glycosylation efficiency. This provides an example of a means to optimize the glycosylation efficiency of heterologously expressed proteins.

The methods above describe methods to alter the structural aspects of the gene sequence to enhance the expression level of the desired protein product. Alternatively, modification of internal protein sequences to enhance selected epitopes or to remove selected epitopes can be employed to create a more desired product, as in, a protein product that has an altered immunogenic potential. As an example, epitopes in the dengue E protein that are believed to generate flavivirus cross-reactivity antibody responses were altered to reduce the potential of immune enhancement (Hughes et al, 2012). These included the immunodominant B cell epitope of the fusion peptide and domain III epitopes.

While the structure of flavivirus envelope proteins has been well studied and the structures established by cryo-EM and x-ray crystallography, what constitutes an optimal gene sequence for the expression of heterologous proteins in eukaryotic host cell expression systems is not currently well defined. Current technology and methods provide the potential to assemble gene sequences and make modification to internal sequences and define new end points that can lead to improvements in structure and function. While the potential exists to make such modifications, it is common knowledge that not all attempts to do so result in success. The modifications or attempts to optimize that work with one protein and in a given expression system do not always work on other proteins or in other expression systems. For example, the removal of the first 58 amino acids from the N-terminus of the West Nile envelope protein ectodomain abolishes expression. In another example, the expression of the C-terminal domain (domain III) as of the West Nile or Tick-borne encephalitis envelope protein is easily expressed, however, these subunit proteins are suboptimal in their ability to prime functional immune responses, although it is not obvious why this occurs. Therefore, a systematic evaluation is required to determine the potential of various efforts to modify and optimize a given gene sequence such that high levels of high quality heterologous protein are expressed and that such alterations do not negatively impact the desired functional attributes. In the biotechnology field, the ability to efficiently produce recombinant proteins at a favorable cost of goods is a key to success. In order to achieve this goal for a particular protein, in this case the Zika virus envelope protein using the *Drosophila* S2 cell expression system, requires further experimentation to define the parameters that result in optimal expression of a high quality protein product.

The combination of multiple optimizations directed at different aspects of a protein's gene sequence and or structure in an appropriate manner such that an additive benefit is achieved can further enhance the utility of the optimized protein product. In the case of flavivirus envelope proteins, several examples exist of expression of various truncated products as soluble recombinant proteins; however, all of these examples relied on sequences derived from native viral sequences or synthetic versions of the native sequence. No significant efforts have been made to optimize expression and secretion other than work to define the carboxy-terminus of the envelope protein that is best suited for expression of a soluble product. There are no examples of combining multiple optimizations to further enhance the expression and secretion of soluble flavivirus envelope proteins. Therefore, the technical problems to be solved are: (1) identification of translational, posttranslational, or structural components of the envelope protein or associated components that when optimized result in improved expression levels and potentially enhance structural quality of the protein such that it is a more potent immunogen; (2) the design of synthetic of component where possible to aid in the optimization; and (3) determining the optimal combination of multiple components such that the combination results in an additive increase in the productivity and quality of protein expression. Further improvements in the expression of the Zika envelope protein could potentially provide for effective immunogens at an improved cost of goods which would bolster the ability to manufacture recombinant proteins suitable for use in vaccines to combat the spread of the Zika virus. The use of such improvements could also be applied to other members of the flavivirus family, including but not limited to West Nile virus, dengue virus, tick-borne encephalitis virus, yellow fever virus, Zika virus and several other viruses which may cause encephalitis, en.wikipedia.org/wiki/Flavivirus-cite_note-ShiP-Y-2 as well as insect-specific flaviviruses (ISFs) such as cell fusing agent virus (CFAV), Palm Creek virus (PCV), and Parramatta River virus (PaRV).

SUMMARY OF THE INVENTION

The invention provides optimized expression of a soluble ZIKV envelope recombinant subunit protein that results in high levels of expression of a native-like or biological relevant protein; and is therefore, an effective immunogen for the production of neutralizing antibodies. Specifically, the invention is directed to expression of the optimized ZIKA gene sequences when Drosophila melanogaster S2 cells are used as the host cell.

The optimized ZIKV gene sequence for expression of a soluble and stable envelope protein is composed of a prM-E contiguous sequence that has been codon optimized, that contains an optimized secretion signal for the E protein segment, and that has an optimized C-terminus that enhances expression and stability of the expressed E product. The optimized gene sequence is contained in an expression vector for use in Drosophila S2 cells. The codon optimization of the gene sequence is designed for optimal expression in Drosophila S2 cells. The synthetic optimized secretion signal that is utilized is designed to result in effective post-translation processing at the pM-E junction by host cell signal peptide protease. The newly defined C-terminal end for the envelope protein, Glycine$_{436}$, provides for interaction between the domain III region and the domain I region that helps to stabilize the expressed and secreted ZIKA envelope protein. The combination of the optimization methods has resulted in a unique gene sequence that provides for the expression of a soluble Zika envelope protein with enhanced stability and at high levels. This improved Zika envelope protein is suitable for use as a vaccine to protect against disease caused by Zika virus infection.

The optimized ZIKV gene sequences of the present invention are capable of high level expression and secretion of the encoded envelope protein into the culture medium of transformed S2 cells. Specifically, the described ZIKV envelope gene sequence has been optimized for 1) codon usage in Drosophila S2 cells, 2) a synthetic, optimized secretion signal sequence and processing site, and 3) a C-terminal truncation point that adds stability to the expressed product.

The invention also provides methods for utilizing the products encoded by the optimized ZIKV gene sequences in vaccine formulations for protecting against disease caused by infection with ZIKV.

One aspect of the present invention is to provide an expression vector that includes a codon optimized DNA sequence encoding a Zika virus pre-membrane and envelope protein. The expression of the DNA sequence results in secretion of a soluble envelope protein in the culture medium.

In one embodiment, the codon optimized DNA sequence includes SEQ ID NO:1.

In another embodiment, the codon optimized DNA sequence is further optimized to enhance secretion of the soluble envelope protein by optimizing the E protein secretion signal sequence. This improved secretion signal codon optimized sequence includes SEQ ID NO:2.

In another embodiment, the codon optimized DNA sequence is further optimized to expression of the soluble envelope protein the carboxy-terminus has been extended to stabilize the expressed envelope protein. This extended codon optimized sequence includes SEQ ID NO:3.

In another embodiment, the codon optimized DNA sequence is further optimized to combine the improved E secretion signal the extended carboxy-terminus to enhance the expression and secretion of the soluble envelope protein. This codon optimized sequence with combined improvements includes SEQ ID NO:4.

In another embodiment, the Drosophila expression vector pHH202 that includes SEQ ID NO:1, SEQ ID NO:2, SEQ ID NO:3, or SEQ ID NO:4 is used to express and secrete the encoded heterologous ZIKV E protein from cultured insect cells. This expression cassette of the pHH202 vector includes SEQ ID NO:7.

In one embodiment, the expression vectors are used in Drosophila cells.

In another embodiment, the expression vectors are used in Drosophila S2 cells.

In one embodiment, the invention provides a vaccine comprising an effective amount of purified Zika virus envelope protein (E), wherein the protein is secreted into the growth medium when expressed recombinantly in a host cell; and an effective amount of aluminum-based adjuvant, wherein the vaccine induces the production of neutralizing antibodies in human subjects. In one aspect, the E protein is recombinantly produced and expressed in insect host cells. In one aspect, the E protein is recombinantly produced and expressed in Drosophila melanogaster Schneider 2 (S2) host cells. Preferably, the vaccine is in a pharmaceutically acceptable excipient. In one aspect, the E protein is encoded by a nucleic acid sequence beginning at nucleotide 505 of SEQ ID NO:1, SEQ ID NO:2 SEQ ID NO:3, SEQ ID NO:4, or SEQ ID NO: 5 which correlates with amino acid residue 169 of SEQ ID NO:6.

Another aspect of the present invention is to provide a method to elicit an immune response that provides protection against disease caused by Zika virus. The method includes administering to a subject in need thereof a composition that includes a soluble envelope protein expressed and secreted by an expression vector that includes a codon optimized DNA sequence that includes SEQ ID NO:1, SEQ ID NO:2, SEQ ID NO:3, or SEQ ID NO:4.

In one embodiment, the composition includes an adjuvant to enhance the immune response. The vaccine may further include an effective amount of a saponin adjuvant, for example QS21, an aluminum-based adjuvant (collectively referred to as Alum), for example Alhydrogel®, or a stable oil-in-water emulsion (SE) adjuvant which may include squalene. In embodiments, a TLR-4 agonist is a fully synthetic lipid A (SLA) derivative. In one embodiment, the vaccine includes a mixture of SLA and a saponin-based adjuvant, such as QS21, wherein the mixture is a liposomal formulation with these adjuvant components (SLA-LSQ).

Other aspects and advantages of the invention will be apparent from the following description and the appended claims.

BRIEF DESCRIPTION OF THE DRAWINGS

FIG. 1 shows pre-membrane and envelope sequence of Zika virus French Polynesia strain H/PF/2013 (SEQ ID NO:5) with translation (SEQ ID NO:6)

FIG. 2 shows codon optimized pre-membrane and envelope (80E) sequence of Zika virus (SEQ ID NO:1)

FIG. 4 shows a comparison of flavivirus secretion signals at the prM-E junction along with an optimized synthetic secretion signal for expression of the Zika virus envelope protein (SEQ ID NOS: 8-21).

FIG. 5 is an alignment of flavivirus envelope proteins at the 80E junction (SEQ ID NOS: 22-37).

FIGS. 6A-6B show ELISA titration results from mice serum following two or three doses of ZIKFP-80E-CoOp formulated with multiple adjuvants.

FIGS. 7A-7B show PRNT titration results from mice serum following two or three doses of ZIKFP-80E-CoOp formulated with multiple adjuvants.

DETAILED DESCRIPTION OF THE INVENTION

Figure 3:
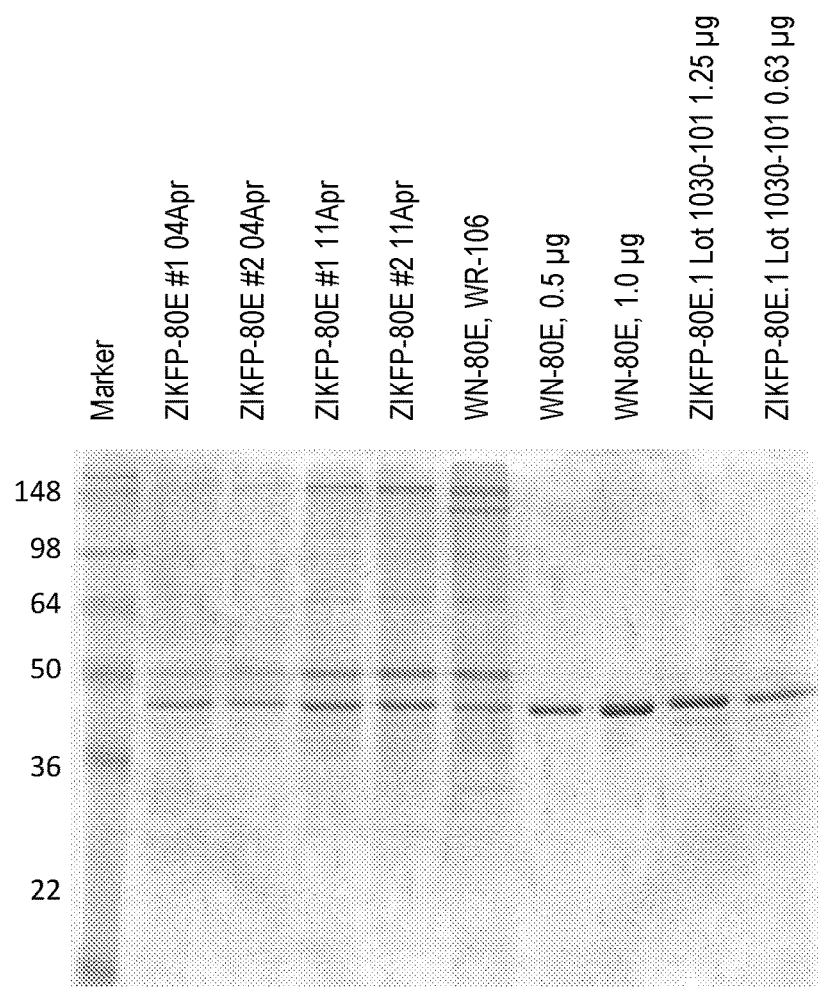
FIG. 3 shows expression of codon optimized ZIPFP-80E-CoOp in Drosophila S2 cells. Samples were run on 10% SDS PAGE gel under non-reducing conditions and stained with Coomassie Blue.

The invention provides an optimized ZIKV gene sequence for expression of a soluble and stable envelope protein that is composed of a prM-E contiguous sequence that has been codon optimized, contains an optimized secretion signal for the E protein segment, and has an optimized C-terminus that enhances expression and stability of the expressed E product. The optimized gene sequence is inserted into a *Drosophila* S2 cell expression vector which drives the expression of high levels of high quality Zika envelope protein in S2 cells that have been stably transformed with the expression vectors carrying the optimized gene sequence. The use of the optimized gene sequence results in an increase in the productivity and quality of the expressed Zika envelope protein. The enhanced expression of the Zika envelope protein provides for an effective immunogen at an improved cost of goods which can bolster the ability to manufacture recombinant proteins suitable for use in vaccines to combat the spread of the Zika virus.

The term "gene sequence" refers to a sequence of DNA that is transcribed into an RNA molecule that may function directly or be translated into an amino acid chain.

The term "optimized" refers to sequences that were derived from naturally occurring sequences and have been altered to enhance their functions.

The term "codon optimized" refers to a nucleic acid coding region that has been adapted for expression in the cells of a given host by replacing at least one, or more than one, or a significant number, of codons with one or more codons that are more frequently used in the genes of that host.

The term "synthetic" refers to sequences that are not found to occur naturally. More specifically, the synthetic elements described herein are not found in the gene sequences of Zika virus or related flaviviruses.

The term "operably linked" refers to a juxtaposition wherein the components so described are in a relationship permitting them to function in their intended manner.

"Expression cassette" means the combination of promoter elements with other transcriptional and translational regulatory control elements which are operably linked to a gene sequence to be expressed. A gene sequence can be inserted into the expression cassette for the purpose of expression of said gene sequence. The expression cassette is capable of directing transcription which results in the production of an mRNA for the desired gene product which is then translated to protein by the host cell translational systems. The expression cassette is integral to the expression vector (plasmid). Such an expression vector directs expression of the protein encoded by the gene sequence once introduced into host cells.

The term "transformed" refers to the DNA-mediated transformation of cells. This refers to the introduction of plasmid DNA into insect cells in the process of generating stable cell lines following the integration of the introduced DNA into the genome of the cells. This term is used in place of the term "transfection" which is often used in the same context. The term transformation is used for the introduction of plasmid DNA to cultured cells to distinguish from the introduction of viral DNA into cultured cells which was originally referred to as transfection. As there are no viral DNA sequences in the present invention which are introduced into the host that results in the production of virus-like particles or cell lysis the term transformed is preferred.

"Expression" or "expressed" means the production of proteins using expression vectors and host cells, for instance, *Drosophila* S2 cells to produce a recombinant protein product that is readily detectable as a cell associated product or as a secreted product in the culture medium.

"Secretion" means secretion of an expressed recombinant protein from cultured host cells into culture medium. The expressed and secreted protein is the result of a given gene sequence being operably linked to an expression cassette such that the sequence codes for the given protein.

The term "product" refers to any recombinant protein, full length or subunit thereof, which is expressed by a host cell into which an expression vector carrying the gene sequence encoding the product has been introduced.

Insect cells are an alternative eukaryotic expression system that provide the ability to express properly folded and post-translationally modified proteins while providing simple and relatively inexpensive growth conditions. The use of stably transformed insect cell expression systems provide benefits over those based on baculovirus infection of the host insect cells. On this basis, S2 cells were selected as the insect host cells of choice. As a result, the efforts to optimize the expression vectors for stably transformed insect cells were based on data derived from the analysis of specific *Drosophila* genes as well as the complete *Drosophila* genome.

In a preferred embodiment of the invention, the E protein secretion signal located at the carboxy end of the prM sequence and immediately preceding the E sequence N-terminus, is a synthetic sequence designed to enhance the processing of these sequences. This synthetic secretion sequence has an increase core hydrophobic region and the −2 and −1 amino acid residues have been optimized to increase the recognition of the signal protease cleavage site at the prM-E junction. The amino acid residues at +1 and +4 of the E sequence have also been optimized to aid in the recognition of the signal protease cleavage site. The amino acid sequence of the synthetic secretion signal including the optimized residues in the E sequence are shown in FIG. 4 and the nucleotide sequence that encodes these elements within the codon optimized prM-80E sequence (Op80E-CoOp) is detailed in SEQ ID NO:2.

In a preferred embodiment of the invention, the C-terminus of the E protein has been extended beyond the 80E terminus has been extended to stabilize the soluble envelope protein that is expressed. Specifically, the C-terminus of the soluble E protein has been extended from Gly-404 to Ile-436 as shown in FIG. 5. The codon optimized prM-E nucleotide sequence that encodes the extended C-terminal E protein (E-436-CoOp) is detailed in SEQ ID NO:3.

In a more preferred embodiment of the invention, the combination of the optimized and synthetic elements have been combined into a single gene sequence for the expression of the Zika envelope protein that results in an enhanced efficiency and yield of the product. The product is also enhanced in terms of stability as a soluble product and as an immunogen for use as a vaccine. The prM-E nucleotide sequence containing the assembled optimized Zika virus envelope protein components, codon optimization, synthetic secretion signal, and the E-436 C-terminal extension (OpE-436-CoOp) is presented in SEQ ID NO:4.

Thus, the present invention provides the combination of multiple optimizations directed at different aspects of the Zika virus prM-E gene sequence in such a manner that an additive benefit is achieved and results in high levels of the envelope protein being expressed. The optimized Zika prM-E sequence when used to express the envelope protein in *Drosophila* S2 cells results in the economic production of large quantities of high quality proteins. The Examples below show that using the individual optimized elements in the Zika gene sequence results in improved or enhanced expression of the envelope protein. The highest levels of envelope protein expression are achieved in the gene sequence in which all of the identified optimized elements are combined.

Although the descriptions presented above and the examples that follow are primarily directed at the use of the optimized expression vectors with *Drosophila* S2 cells, the vectors and methods can be applied to other insect cell lines that result in stable cell lines following transformation of host cells with plasmid DNA.

The following examples are offered by way of illustration and not by way of limitation.

EXAMPLES

The following examples describe the development of the optimized ZIKV gene sequences for the expression of the envelope protein in insect cells. The examples demonstrate the ability to effectively express the proteins in *Drosophila* S2 cells at levels that are commercially suitable for product development.

The examples demonstrate the ability of the individual regulatory elements to enhance the ability to express proteins in S2 cells and the efforts made to determine what changes contributed to the enhanced function of these elements. The results presented below demonstrate that different elements and modifications of these elements can result in high levels of expression or in very little or no detectable expression. Thus, the selection of functional and effective regulatory elements must be determined thorough experimentation. Hence, the invention described herein is unique in that the expression cassette described is mostly synthetic in composition and directs high levels of protein expression.

Example 1

Expression of Wild Type and Codon Optimized ZIKV 80E Proteins in *Drosophila* S2 Cells In an effort to identify optimized gene sequences for driving high levels of high quality ZIKV envelope protein in S2 cells, the wild type prM-E gene sequence was compared to a codon optimized prM-E gene sequence. Both the WT and codon optimized sequences were produced synthetically (DNA2.0, Menlo Park, Calif.). For codon optimization, the standard *Drosophila melanogaster* codon table was used (Kazusa DNA Research Institute, kazusa.or.ip/codori/). As the objective is to improve the efficiency of expression, which is in part controlled by the translation process, a threshold of 10% usage was used in assigning codons (any codon that is used <10% is excluded). Additionally, based on our analysis of highly expressed proteins in *Drosophila*, we have added the exclusion of the following codons, CGA for Arg, ATA for He, and GTA for Val. The synthesized gene sequences included appropriate restriction enzyme sites at the ends and a stop codon was included at the end of the envelope protein coding region.

For the expression of the ZIKV envelope protein, the genomic sequence representing the ZIKV pre-membrane protein and carboxy-truncated envelope protein (prM-80E) is used. The sequence utilized for expression is based on the 2013 French Polynesia strain H/PF/2013, (GenBank Accession #KJ776791). The WT 2013 French Polynesia strain H/PF/2013 prM-80E sequence along with translation is provided in FIG. 1. The codon optimized sequence is detailed in SEQ ID NO:1 and FIG. 2. While the sequence of the codon optimized sequence is different, it codes for the same protein sequence provided in FIG. 1 for the WT sequence. Viral strains in the Asian lineage such as the 2013 French Polynesia strain H/PF/2013 are responsible for the ongoing outbreak in the Americas (22). The first amino acid codon of the prM sequence is fused in frame with the secretion signal of the expression vector. When the prM-80E sequence is expressed in the S2 cells, the prM-E junction is processed by an S2 encoded signal protease. This results in the secretion of an 80E product with a native N-terminus into the culture medium.

The synthetic DNA fragments were digested with appropriate restriction enzymes and inserted with in the expression cassette (SEQ ID NO:7) of the pHH202 expression vector that has been digested with Nhe I and Xho I. The pHH202 expression cassette contains the following elements: metallothionein promoter, optimized Kozak sequence, influenza HA secretion signal, and the SV40 early 3'UTR. The hygromycin encoding gene is also incorporated into the pHH202 expression plasmid downstream of the expression cassette. The pHH202 expression plasmid is designed to allow directional cloning of the gene of interest into unique Nhe I and Xho I sites. The junctions and full inserts of all constructs were sequenced to verify that the various components that have been introduced are correct and that the proper reading frame has been maintained.

For this work standard methods of culturing and transformation of S2 cells were utilized (Van der Straten, *Methods in Mol. and Cell Biol.* (1989) 1:1-8; Culp et al., *Biotechnology* (1991) 9:173-177; Kirkpatrick and Shatzman, In *Gene Expression Systems: Using Nature for the Art of Expression*, Eds. Fernandez and Hoeffler, Academic Press, (1999) 289-330). *Drosophila* S2 cells (Schneider, *J. Embryol. Exp. Morph.* (1972) 27:353-365) obtained from ATCC were utilized. The S2 cells have been adapted to growth in Excell 420 medium (SAFC, St Louis, Mo.) and all procedures and culturing described herein were in Excell 420 medium. Cultures are typically seeded at a density of $1 \times 10^6$ cells/ml and are passed between days 5 and 7. All cultures were incubated at 26° to 27° C. Expression plasmids into which genes of interest were inserted were transformed into S2 cells using the ExpreS2 TR reagent (Expres2ion Bio, Horsholm, Denmark). Following transformation, cells resistant to hygromycin B, 0.3 mg/ml, were selected. Once stable cell lines were selected, they were evaluated for expression of the appropriate products. For the evaluation of expression, 5 ml cultures of selected cell lines were seeded at $2 \times 10^6$ cells/ml and cultured in the presence of 0.2 mM copper sulfate at 26° C. for 7 days. Cultures were evaluated for expression of recombinant proteins in both the cell associated fractions and the culture medium. Proteins were separated by SDS-PAGE and either stained with Coomassie blue or blotted onto nitrocellulose for Western blot analysis. Expression levels ≥1 µg/ml (1 mg/L) are readily detected in S2 cultures by Coomassie staining of SDS-PAGE gels.

Parental S2 cell lines expressing the ZIKFP 80E-WT and ZIKFP-80E-CoOp have been established using standard methods developed at HBI (23). The expression of the ZIKFP-80E products has been identified using the conformationally sensitive monoclonal antibody (mAb) 4G2 that recognizes most flavivirus envelope proteins (24). The expression data for two parental S2 cell lines expressing codon optimized ZIKFP-80E-CoOp is shown in FIG. 3. West Nile 80E (WN-80E) is included for comparison. The 4G2 mAb is also used for purification utilizing immunoaffinity chromatography (IAC) methods. The 4G2 mAb based IAC purification is analogous to the process that is currently utilized for the WN-80E vaccine program and has been successfully transferred to cGMP manufacturing.

The use of the codon optimized prM-E gene sequence in transformed S2 resulted in the expression ZIKFP-80E-CoOp at approximately 30 µg/ml. A coomassie stained SDS-PAGE gel is shown in FIG. 3 with both unconcentrated culture media samples with ZIKFP-80E-CoOp (lanes 2-5) and purified ZIKFP-80E-CoOp (lanes 9-10). WN-80E samples are also included on the gel for comparison.

Another adjuvant which may be utilized in the presently described vaccine formulation is a stable oil based emulsion. In one embodiment the emulsion is a stable oil-in-water emulsion (SE) which may optionally include squalene.

Another adjuvant which may be utilized in the presently described vaccine formulation is a saponin-based adjuvant, such as QS21. QS21 is a purified plant extract that enhances the ability of the immune system to respond to vaccine antigens. It is derived from the Soap bark tree (*Quillaja saponaria*) and contains water soluble triterpene glucoside compounds, which are members of a family of plant-based compounds called saponins. In one embodiment, a saponin-based adjuvant is combined with SLA forming a liposome formulation. In one embodiment, SLA is combined with QS21 to form a liposome formulation (SLA-LSQ).

The vaccine formulation of the present invention may further include one or more additional pharmaceutically acceptable diluents, carriers, solubilizers, emulsifiers, preservatives and/or adjuvants.

Example 2

Design of Synthetic Secetion Signal Sequence for Enhanced Expression in *Drosophila* S2 Cells The secretion signal peptide plays an important role in the expression of proteins that are targeted for secretion from the cell. Therefore, the use of optimal sequences that target the desired recombinant protein for secretion into the culture medium during production is important to the efficiency of processing the protein and potentially increasing the yield of the product. The example of secretion signal optimization presented by Zhang et al. (*J. Gene Med*. (2005) 7:354-365) clearly demonstrates the benefits of secretion signal optimization. However, this specific example applies to plants and it is not clear that the changes to the secretion signal described apply to other eukaryotic cell types. Furthermore, as Zika envelope expression is achieved through the expression of the prM-E polypeptide, the secretion is directed by the integral sequence of the prM protein that serves as a component of the transmembrane anchor for the prM protein. The second membrane spanning sequence of the prM protein also serves as the secretion signal peptide for the E protein. No clear guidance exists on how to best optimize this transmembrane anchor/secretion signal peptide sequence to improve the secretion and yield of the envelope protein. Therefore, a survey of flavivirus prM-E secretion signals was conducted. The putative secretion signals from prM and the E protein N-terminus were analyzed using the SignalP program described by Petersen et al (*Nat. Methods*, (2011) 8(10): 785-6), which predicts the strength of the secretion signal based on an established algorithm and also predicts the cleavage site of the sequence analyzed.

Surprisingly, as shown in FIG. 4, the prediction scores for all of the flaviviruses analyzed were poor. A score of ≥0.500 is defined as a good secretion signal. Therefore, an effort was made to establish the changes required to improve the score of the predicted secretion signal peptide. Such changes are believed to result in an increased expression of the desired protein product into the culture medium of stably transformed S2 cells. The designs of the synthetic secretion signal followed the matrix table first described by von Heijne (*Nuc. Acids Res*. (1986) 14:4683-4690), and further refined by Bendtsen et al. (*J. Mol. Biol*. (2004) 340:783-795). The design was to maintain the length of the secretion signal at 17 amino acids, and include a single charged residue in the basic region, improve the hydrophobic region, and improve the −1 and −2 positions. Initially, only the secretion signal was designed (SyntheticZ) leaving the N-terminus of the E protein unaltered. However, the score returned for this sequence was only 0.374 despite the optimization. The +1 through +4 amino acids (in this case the E protein N-terminus) can also impact the efficiency of the cleavage site; therefore, this was also altered at the +1 and +4 positions. The combination of the synthetic secretion sequence and the changes at +1 and +4 (Synthetic+) resulted in a score of 0.649. Thus, the combination of the two changes was required to achieve a score of ≥0.500. To confirm that both changes are required only the +1 and +4 changes were made to the WT Zika sequence (Zika+) and analyzed. This resulted in a slight improvement in the score from 0.231 to 0.310, but still below a score of 0.500. The amino acid sequences of the signal peptides described are listed below along with their Signal P scores.

```
                  -1+1
                   | |
QKVIYLVMILLIAPAYS IRCIGV "Zika"      Score: 0.231

MRTIIALLLLLVSGAHG IRCIGV "SyntheticZ" Score: 0.374

MRTIIALLLLLVSGAHA SRCVGV "Synthetic+" Score: 0.703

QKVIYLVMILLIAPAYS SRCVGV "Zika+"      Score: 0.310
```

The Synthetic+ secretion signal is operatively linked to the prM-80E codon optimized Zika sequence (SEQ ID NO:1) to create the combination of codon optimization and secretion signal optimization as detailed in SEQ ID NO:2. SEQ ID NO:2 is then inserted into the expression cassette (SEQ ID NO: 7) of the pHH202 vector. The expressed and secreted E protein is referred to as ZIKFP-Op80E-CoOp.

Example 3

Alteration of the Carboxy-Terminus of the E Protein Sequence to Enhance Secretion and Stability The C-terminus of the flavivirus E ectodomain is typically defined by the Gly residue in the sequence motif W-X-K/

R-X-G. In the case of Zika this is $Gly_{404}$. While this truncation results in secretion of the ZIKFP-80E product as shown in Example 1, efforts to improve the stability of the expressed E protein, both in terms of expression levels and structural integrity are desirable. An analysis of the Zika virus cyro EM data (Sirohi et al, 2016) suggests that an extension of the E ectodomain from $Gly_{404}$ to $Gly_{436}$ may provide a stabilizing effect. The extension of the C-terminus to $Gly_{436}$ has the potential to provide for interaction between the domain III region and the domain I region and help to stabilize the expressed and secreted ZIKV envelope protein. In the extended E protein, the $Phe_{431}$ residue has the potential to interact with a hydrophobic pocket in domain I composed of $Val_{12}$, $Val_{23}$ and $Val_{24}$. An extension of the E protein in this manner could lead to enhancement of proper protein folding (native-like structure) and stability.

Example 4

Immunogenic Evaluation of Codon Optimized ZIKFP-80E Protein in Mice

The immunogenicity of the *Drosophila* S2 expressed ZIKFP-80E-CoOp subunit protein was evaluated in both inbred and outbred mice with several different adjuvants to assess the immunogenic potential. Mice were immunized intra-muscularly with either two doses or 3 doses of ZIKFP-80E separated by 3 week intervals. Two amounts of ZIKFP-80E-CoOp were evaluated, 5.0 µg and 2.5 µg. The adjuvants tested were Alhydrogel, GPI-0100 and GLA-SE. Mice were bled 2 weeks after the 2 or third dose to prepare serum samples for antibody analysis. The design of the immunogenicity study is presented in Table 1.

TABLE 1

ZIKFP-80E-CoOp Immunogenicity Study Design.

| Group | Test Article | Antigen Dose | Al Elem | GPI-0100 | GLA SE | # SW Mice | # 129 Mice | # Mice 2 dose | # Mice 3 dose |
|---|---|---|---|---|---|---|---|---|---|
| 1 | ZIKFP-80E-CoOp with GPI-0100 Adjuvant in SW | 5 µg | — | 100 µg | — | 10 | — | 5 | 5 |
| 2 | ZIKFP-80E-CoOp with Alum Adjuvant in SW | 5 µg | 120 µg | — | — | 10 | — | 5 | 5 |
| 3 | ZIKFP-80E-CoOp with GLA-SE Adjuvant in SW | 5 µg | — | — | 5 µg | 10 | — | 5 | 5 |
| 4 | ZIKFP-80E-CoOp with GLA-SE Adjuvant in SW | 2.5 µg | — | — | 5 µg | 10 | — | 5 | 5 |
| 5 | No Antigen (Negative Control) GLA-SE Adjuvant in SW | — | — | — | 5 µg | 5 | — | 2 | 3 |
| 6 | ZIKFP-80E-CoOp with GPI-0100 Adjuvant in 129S6/SvEvTac | 5 µg | — | 100 µg | — | — | 10 | 5 | 5 |
| 7 | ZIKFP-80E-CoOp with GLA-SE Adjuvant in 129S6/SvEvTac | 5 µg | — | — | 5 µg | — | 10 | 5 | 5 |
| 8 | ZIKFP-80E-CoOp with GLA-SE Adjuvant in 129S6/SvEvTac | 2.5 µg | — | — | 5 µg | — | 10 | 5 | 5 |
| 9 | No Antigen (Negative Control) GLA-SE Adjuvant in 129S6/SvEvTac | — | — | — | 5 µg | — | 5 | 2 | 3 |

The codon optimized Zika prM-E sequence that extends the E protein to amino acid residue 436 is referred to as prM-E-436 and is detailed in SEQ ID NO:3. SEQ ID NO:3 is then inserted into the expression cassette (SEQ ID NO: 7) of the pHH202 vector. The expressed and secreted E protein is referred to as ZIKFP-E-436-CoOp.

Figure 8:
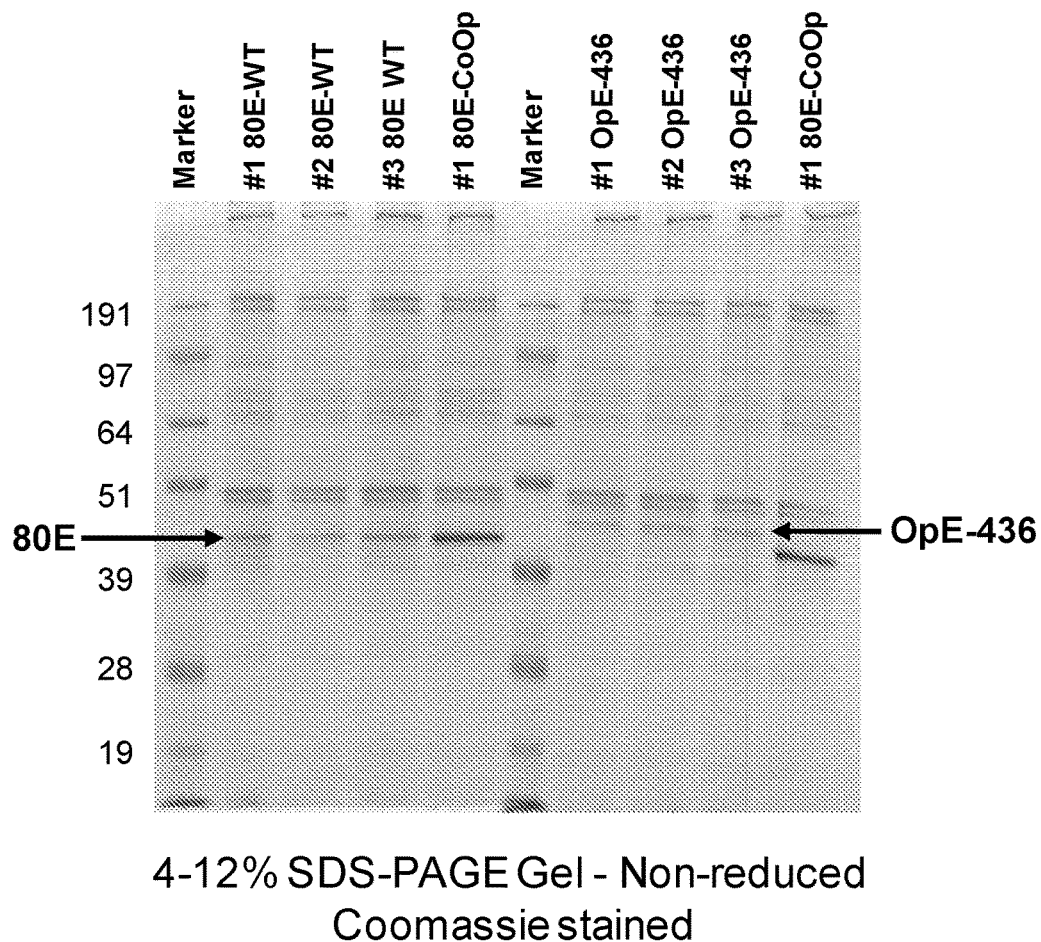
FIG. 8 shows expression of ZIPFP-80E-WT, ZIKFP-80E-CoOp and ZIKFP OpE-436-CoOp in *Drosophila* S2 cells. Samples were run 10% SDS PAGE gel under non-reducing conditions and stained with Coomassie Blue.

A fully optimal Zika prM-E sequence that combines the three features, codon optimization, optimized synthetic secretion signal, and the extended E sequence was also generated as detailed in SEQ ID NO:4. SEQ ID NO:4 is then inserted into the expression cassette (SEQ ID NO: 7) of the pHH202 vector. The expressed and secreted E protein is referred to as ZIKFP-OpE-436-CoOp. The expression and secretion of the ZIKFP-80E-WT, ZIKFP-80E-CoOp, and ZIKFP-OpE-436-CoOp from S2 cells was evaluated by SDS-PAGE. A coomassie stained gel is shown in FIG. 8. All samples represent unconcentrated culture media to allow for direct comparison of the expression levels between the different recombinant Zika E proteins. While expression is detected for each of the expressed sequences, ZIKFP-80E-WT, ZIKFP-80E-CoOp, and ZIKFP-OpE-436-CoOp, the ZIKFP-80E-CoOp results in the highest level of expression.

Mice were immunized intra-muscularly two or three times at 3 week intervals with the purified subunit protein at a dose of 5.0 µg or 2.5 µg. Five mice were bled two weeks after dose two and 5 mice were bled two weeks after dose three. The sera were then assessed for anti-80E antibody titers by ELISA. The sera were also evaluated for virus neutralizing antibodies using the plaque reduction neutralization test (PRNT).

The ELISA results for the serum collected following two or three doses of ZIKFP-80E-CoOp formulated with multiple adjuvants is presented in FIG. 6. The results of the ELISA indicate that the ZIKFP-80E-CoOp is immunogenic and the responses in the 129S6/Sv mice is more robust and consistent than in the Swiss Webster mice.

REFERENCES

The following references are each relied upon and incorporated herein in their entirety.

Bendtsen J D, Nielsen H, von Heijne G, Brimal S. Improved prediction of signal peptides: SignalP 3.0. J Mol Biol 2004; 340:783-795.

Bernard A R, Kost T A, Overton L, Cavegn C, Young J, Bertrand M, Yahia-cherif Z, Chabert C and Mills A.

Recombinant protein expression in *Drosophila* cell line: comparison with the baculovirus system. Cytotechnology. 1994; 15: 139-144.

Bin L, Tsing S, Kosaka A H, Nguyen B, Osen E G, Bach C, Chan H and Barnett J. Expression of human dopamine B-hydroxylase in *Drosophila* Schneider 2 cells. Biochem. J. 1996; 313: 57-64.

Culp J S, Johansen H, Hellmig B. Regulated expression allows high level production and secretion of HIV gp120 envelope glycoprotein in *Drosophila* Schneider cells. Biotechnology. 1991; 9: 173-177.

Dick G W, Kitchen S F, Haddow A J. Zika virus. I. Isolations and serological specificity. Trans R Soc Trop Med Hyg. 1952; 46(5): 509-20. Duffy M R, Chen T H, Hancock W T, Powers A M, Kool J L, Lanciotti R S, Pretrick M, Marfel M, Holzbauer S, Dubray C, Guillaumot L, Griggs A, Bel M, Lambert A J, Laven J, Kosoy O, Panella A, Biggerstaff B J, Fischer M, Hayes E B. Zika virus outbreak on Yap Island, Federated States of Micronesia. N Engl J Med. 2009; 360(24):2536-43. Gardsvoll H, Werner F, Sondergaard L, Dano K, Ploug M. Characterization of low-glycosylated forms of soluble human urokinase receptor expression in *Drosophila* Schneider 2 cells after deletion of glycosylation-sites. Protein Expression and Purification. 2004; 34:284-295.

Farrell P J, Lu M, Prevost J, Brown C, Behie L, Iatrou K. High-level expression of secreted glycoproteins in transformed lepidopteran insect cells using a novel expression vector. Biotechnology and Bioengineering. 1998; 60(6): 656-663.

Gustafsson C, Govindarajan S, Minshull J. 2004. Codon bias and heterologous protein expression. Trends Biotechnol. July; 22(7):346-53.

Hofmann K J, Schultz L D. Mutations of the a-galactosidase signal peptide which greatly enhance secretion of heterologous proteins by yeast. Gene. 1991; 101: 105-111.

Hughes H R, Crill W D, Chang G J. Manipulation of immunodominant dengue virus E protein epitopes reduces potential antibody-dependent enhancement. Virol J. 2012 Jun. 18; 9: 115. Ikonomou L, Schneider Y-J, Agathos S N. Insect cell culture for industrial production of recombinant proteins. Appl. Microbiol. Biotechnol. 2003; 62: 1-20.

Incardona, J. P. and T. L. Rosenberry. Construction and characterization of secreted and chimeric transmembrane forms of *Drosophila* acetylcholinesterase: a large truncation of the C-terminal signal peptide does not eliminate glycoinositol phospholipid anchoring. Mol. Biol. of the Cell 1996; 7:595-611.

Ivey-Hoyle, M. Recombinant gene expression in cultured *Drosophila melanogaster* cells. Curr. Opin. Biotechnol. 1991; 2:704-707.

Johansen H A, van der Straten R, Sweet R, Otto E, Maroni G, Rosenberg M. Regulated expression at high copy number allows production of a growth-inhibitory oncogene product in *Drosophila* Schneider cells. Genes and Development. 1989; 3: 882-889.

Kirkpatrick R B and Shatzman A. *Drosophila* S2 System for heterologous gene expression. In Gene Expression Systems: Using Nature for the Art of Expression. Joseph M Fernandez and James Hoeffler editors. Academic Press. 1999; Pp. 289-330.

Le Loir Y, Azevedo V, Oliveira S C, Freitas D A, Miyoshi A, Bermudez-Humaran L G, Nouaille S, Ribeiro L A, Leclercq S, Gabriel J E, Guimaraes V D, Oliveira M N, Charlier C, Gautier M, Langella P. Protein secretion in *Lactococcus lactis*: and efficient way to increase the overall heterologous protein production. Microb. Cell Fact. 2005; 4:2.

Mellquist J L, Kasturi L, Spitalnik S L, Shakin-Eshleman S H. The amino acid following an asn-X-Ser/Thr sequon is an important determinant of N-linked core glycosylation efficiency. Biochemistry. 1998 May 12; 37(19):6833-7.

Modis Y, Ogata S, Clements D, Harrison S C. A ligand-binding pocket in the dengue virus envelope glycoprotein. Proc. Natl. Acad. Sci. USA. 2003; 100:6986-6991.

Modis Y, Ogata S, Clements D, Harrison S C. Structure of the dengue virus envelope protein after membrane fusion. Nature. 2004; 427(6972): 313-319.

Oehler E, Watrin L, Larre P, Leparc-Goffart I, Lastere S, Valour F, Baudouin L, Mallet H, Musso D, Ghawche F. Zika virus infection complicated by Guillain-Barre syndrome—case report, French Polynesia, December 2013. Euro Surveill. 2014; 19(9). Olsen M K, Rockenbach S K, Fischer H D, Hoogerheide J G, Tomich C S C. Stable production of an analog of human tissue plasminogen activator from cultured *Drosophila* cells. Cytotechnology. 1992; 10: 157-167.

PAHO. Countries and territories with autochthonous transmission in the Americas reported in 2015-2016 2016 [cited 2016 Feb. 14]. Available from: paho.org/hq/index.php?option=com_content&view=article&id=11603&Ite mid=41696&lang=en.

PAHO. Cumulative Zika Vims Cases in the Americas 2016 [cited 2016 Apr. 2]. Available from: ais.paho.org/phip/viz/ed_zika_cases.asp.

Petersen T N, Brunak S, von Heijne G, Nielsen H. SignalP 4.0: discriminating signal peptides from transmembrane regions. Nat Methods. 2011 Sep. 29; 8(10):785-6

Schmetzer O, Moldenhauer G, Riesenberg R, Pires J R, Schlag P, Pezzutto A. 2005. Quality of recombinant protein determines the amount of autoreactivity against the tumor-associated epithelial cell adhesion molecule antigen: low frequency of antibodies against the natural protein. The Journal of Immunology. 2005; 174: 942-952.

Schmidt F R. Recombinant expression systems in the pharmaceutical industry. Appl Microbiol Biotechnol. 2004; 65:363-372. Schneider I J. Cell lines derived from late embryonic stages of *Drosophila melanogaster*. J. Embryol. Exp. Morph. 1972; 27:353-365.

Schuler-Faccini L, Ribeiro E M, Feitosa J J V I, Horovitz D D, Cavalcanti D P, Pessoa A, Doriqui M J, Neri J I, Neto J M, Wanderley H Y, Cernach M, El-Husny A S, Pone M V, Serao C L, Sanseverino M T, Brazilian Medical Genetics Society-Zika Embryopathy Task F. Possible Association Between Zika Vims Infection and Microcephaly-Brazil, 2015. MMWR Morb Mortal Wkly Rep. 2016; 65(3):59-62.

Tognarelli J, Ulloa S, Villagra E, Lagos J, Aguayo C, Fasce R, Parra B, Mora J, Becerra N, Lagos N, Vera L, Olivares B, Vilches M, Fernandez J. A report on the outbreak of Zika vims on Easter Island, South Pacific, 2014. Arch Virol. 2015.

van der Straten A H, Johansen H, Rosenberg M, Sweet R W. Introduction and constitutive expression of gene products in cultures of *Drosophila* cells using hygromycin B selection. Methods in Mol And Cell Biol. 1989; 1: 1-8.

von Heijne G. A new method for predicting signal sequence cleavage sites. Nuc Acids Res. 1986; 14:4683-4690.

WHO. WHO statement on the first meeting of the International Health Regulations (2005) (THR 2005) Emergency Committee on Zika vims and observed increase in neurological disorders and neonatal malformations: WHO;

2016 [cited 2016 Feb. 12]. Available from: who.int/mediacentre/news/statements/2016/1st-emergency-committee-zika/en/.

WHO. Guillain-Barre syndrome—Colombia and Venezuela 2016 [cited 2016 Feb. 14]. Available from: who.int/csr/don/12-february-2016-gbs-colombia-venezuela/en/.

WHO. Guillain-Barre syndrome—El Salvador 2016 [cited 2016 Feb. 14]. Available from: who.int/csr/don/21-january-2016-gbs-el-salvador/en/

WHO. Zika Virus, Microcephaly and Guillain-Barre Syndrome Situation Report: WHO; 2016 [cited 2016 Apr. 2]. Available from: apps.who.int/iris/bitstream/10665/204718/1/zikasitrep_31Mar2016_eng.pdf?ua=1

WHO. Zika Product Landscape 2016 [cited 2016 Apr. 2]. Available from: who.int/csr/research-and-development/zika-rd-pipeline.pdf.

Xu T, Logsdon N J, Water M R. Structure of insect-cell-derived IL-22. Acta Crystallogr D Biol Crystallogr. 2005; 61(pt 7): 942-50.

Zhang L, Leng Q, Mixson A J. Alteration in the IL2 signal peptide affects secretion of proteins in vitro and in vivo. J. Gene Med. 2005; 7:354-365.

```
Codon Optimized Zika prM-80E nucleotide sequence
(Product = ZIKFP-80E-CoOp)
                                                     SEQ ID NO: 1
GCAGAAGTGACCCGCCGCGGCAGCGCATACTATATGTACCTCGATCGTAACGACGCGGGC

GAAGCTATCTCCTTCCCGACCACGCTGGGCATGAACAAGTGCTATATTCAGATTATGGAC

CTGGGCCATATGTGCGACGCGACCATGTCCTACGAATGTCCGATGCTGGACGAAGGAGTT

GAGCCTGATGACGTCGATTGCTGGTGCAATACCACTTCCACCTGGGTGGTGTACGGTACT

TGCCATCACAAAAAGGGCGAAGCCCGCCGTTCCCGTCGCGCTGTCACTCTGCCAAGCCAC

AGCACACGCAAATTGCAGACGAGGAGTCAGACGTGGTTGGAGTCGCGCGAGTACACAAAG

CACCTGATTCGGGTGGAAAATTGGATCTTCCGGAATCCGGGCTTTGCTTTGGCGGCAGCC

GCTATTGCGTGGCTGCTCGGCAGTAGCACGTCGCAGAAAGTGATTTACCTGGTCATGATC

CTCCTCATCGCCCCCGCCTATTCGATCCGTTGCATTGGCGTCAGCAACCGCGATTTCGTG

GAGGGCATGAGCGGTGGAACCTGGGTCGACGTTGTGCTGGAACATGGCGGCTGCGTCACA

GTGATGGCTCAGGACAAGCCGACCGTGGACATCGAGTTGGTTACCACGACGGTTTCCAAC

ATGGCGGAGGTTCGCAGCTACTGCTACGAAGCCAGCATCAGCGATATGGCATCGGACAGC

CGGTGCCCGACCCAGGGAGAAGCATATCTCGACAAGCAGTCCGACACGCAATATGTCTGT

AAAAGGACGCTCGTTGACCGCGGCTGGGGCAACGGCTGCGGCCTGTTTGGAAAAGGCTCC

CTGGTCACATGCGCGAAGTTTGCATGTTCGAAGAAGATGACGGGCAAAAGCATCCAACCA

GAGAATCTGGAATACCGGATCATGTTGTCCGTGCACGGCAGCCAGCATAGTGGCATGATT

GTGAACGACACCGGTCACGAAACCGACGAGAACCGCGCTAAAGTTGAGATCACCCCGAAC

AGTCCCCGGGCCGAGGCCACGCTGGGAGGCTTCGGATCGCTGGGTCTGGATTGCGAACCC

CGCACCGGACTGGATTTCTCGGATCTCTACTACCTGACGATGAACAATAAGCACTGGCTG

GTGCACAAAGAGTGGTTCCATGATATCCCATTGCCCTGGCATGCCGGTGCCGATACCGGA

ACACCCCACTGGAACAATAAGGAGGCCCTGGTCGAGTTTAAGGACGCGCACGCTAAGCGT

CAAACGGTGGTGGTGCTGGGATCCCAAGAGGGCGCCGTGCACACGGCCCTGGCCGGCGCG

CTGGAGGCCGAGATGGACGGTGCCAAGGGACGCTTGAGCTCCGGACACCTGAAATGCCGC

CTCAAGATGGACAAGCTGCGTCTGAAAGGAGTGTCCTACTCCCTCTGCACCGCCGCGTTC

ACCTTCACTAAGATTCCCGCCGAGACTTTGCACGGTACAGTGACCGTTGAGGTGCAGTAT

GCCGGAACCGATGGCCCTTGCAAAGTCCCGGCCCAAATGGCGGTGGATATGCAGACGCTG

ACGCCTGTGGGCCGGCTCATTACCGCAAACCCAGTCATCACGGAGAGTACCGAGAACTCG

AAGATGATGCTGGAGTTGGACCCCCCGTTTGGCGACAGTTACATCGTGATCGGAGTGGGC

GAAAAGAAGATTACGCACCATTGGCACCGTAGCGGC
```

Codon optimized nucleotide sequence for Zika prM-80E with synthetic
E secretion signal (Product = ZIKFP-Op80E-CoOp)

SEQ ID NO: 2

GCAGAAGTGACCCGCCGCGGCAGCGCATACTATATGTACCTCGATCGTAACGACGCGGGC

GAAGCTATCTCCTTCCCGACCACGCTGGGCATGAACAAGTGCTATATTCAGATTATGGAC

CTGGGCCATATGTGCGACGCGACCATGTCCTACGAATGTCCGATGCTGGACGAAGGAGTT

GAGCCTGATGACGTCGATTGCTGGTGCAATACCACTTCCACCTGGGTGGTGTACGGTACT

TGCCATCACAAAAAGGGCGAAGCCCGCCGTTCCCGTCGCGCTGTCACTCTGCCAAGCCAC

AGCACACGCAAATTGCAGACGAGGAGTCAGACGTGGTTGGAGTCGCGCGAGTACACAAAG

CACCTGATTCGGGTGGAAAATTGGATCTTCCGGAATCCGGGCTTTGCTTTGGCGGCAGCC

GCTATTGCGTGGCTGCTCGGCAGTAGCACGTCGA*TGCGCACCATCATTGCCCTGCTCTTG*

*CTGCTCGTGAGCGGTGCCCACGCC*AGCCGTTGCGTGGGCGTCAGCAACCGCGATTTCGTG

GAGGGCATGAGCGGTGGAACCTGGGTCGACGTTGTGCTGGAACATGGCGGCTGCGTCACA

GTGATGGCTCAGGACAAGCCGACCGTGGACATCGAGTTGGTTACCACGACGGTTTCCAAC

ATGGCGGAGGTTCGCAGCTACTGCTACGAAGCCAGCATCAGCGATATGGCATCGGACAGC

CGGTGCCCGACCCAGGGAGAAGCATATCTCGACAAGCAGTCCGACACGCAATATGTCTGT

AAAAGGACGCTCGTTGACCGCGGCTGGGGCAACGGCTGCGGCCTGTTTGGAAAAGGCTCC

CTGGTCACATGCGCGAAGTTTGCATGTTCGAAGAAGATGACGGGCAAAAGCATCCAACCA

GAGAATCTGGAATACCGGATCATGTTGTCCGTGCACGGCAGCCAGCATAGTGGCATGATT

GTGAACGACACCGGTCACGAAACCGACGAGAACCGCGCTAAAGTTGAGATCACCCCGAAC

AGTCCCCGGGCCGAGGCCACGCTGGGAGGCTTCGGATCGCTGGGTCTGGATTGCGAACCC

CGCACCGGACTGGATTTCTCGGATCTCTACTACCTGACGATGAACAATAAGCACTGGCTG

GTGCACAAAGAGTGGTTCCATGATATCCCATTGCCCTGGCATGCCGGTGCCGATACCGGA

ACACCCCACTGGAACAATAAGGAGGCCCTGGTCGAGTTTAAGGACGCGCACGCTAAGCGT

CAAACGGTGGTGGTGCTGGGATCCCAAGAGGGCGCCGTGCACACGGCCCTGGCCGGCGCG

CTGGAGGCCGAGATGGACGGTGCCAAGGGACGCTTGAGCTCCGGACACCTGAAATGCCGC

CTCAAGATGGACAAGCTGCGTCTGAAAGGAGTGTCCTACTCCCTCTGCACCGCCGCGTTC

ACCTTCACTAAGATTCCCGCCGAGACTTTGCACGGTACAGTGACCGTTGAGGTGCAGTAT

GCCGGAACCGATGGCCCTTGCAAAGTCCCGGCCCAAATGGCGGTGGATATGCAGACGCTG

ACGCCTGTGGGCCGGCTCATTACCGCAAACCCAGTCATCACGGAGAGTACCGAGAACTCG

AAGATGATGCTGGAGTTGGACCCCCCGTTTGGCGACAGTTACATCGTGATCGGAGTGGGC

GAAAAGAAGATTACGCACCATTGGCACCGTAGCGGC

Codon optimized nucleotide sequence for Zika prM-E-436
(Product = ZIKFP-E-436-CoOp)

SEQ ID NO: 3

GCAGAAGTGACCCGCCGCGGCAGCGCATACTATATGTACCTCGATCGTAACGACGCGGGC

GAAGCTATCTCCTTCCCGACCACGCTGGGCATGAACAAGTGCTATATTCAGATTATGGAC

CTGGGCCATATGTGCGACGCGACCATGTCCTACGAATGTCCGATGCTGGACGAAGGAGTT

GAGCCTGATGACGTCGATTGCTGGTGCAATACCACTTCCACCTGGGTGGTGTACGGTACT

TGCCATCACAAAAAGGGCGAAGCCCGCCGTTCCCGTCGCGCTGTCACTCTGCCAAGCCAC

AGCACACGCAAATTGCAGACGAGGAGTCAGACGTGGTTGGAGTCGCGCGAGTACACAAAG

CACCTGATTCGGGTGGAAAATTGGATCTTCCGGAATCCGGGCTTTGCTTTGGCGGCAGCC

GCTATTGCGTGGCTGCTCGGCAGTAGCACGTCGCAGAAAGTGATTTACCTGGTCATGATC

```
CTCCTCATCGCCCCCGCCTATTCGATCCGTTGCATTGGCGTCAGCAACCGCGATTTCGTG

GAGGGCATGAGCGGTGGAACCTGGGTCGACGTTGTGCTGGAACATGGCGGCTGCGTCACA

GTGATGGCTCAGGACAAGCCGACCGTGGACATCGAGTTGGTTACCACGACGGTTTCCAAC

ATGGCGGAGGTTCGCAGCTACTGCTACGAAGCCAGCATCAGCGATATGGCATCGGACAGC

CGGTGCCCGACCCAGGGAGAAGCATATCTCGACAAGCAGTCCGACACGCAATATGTCTGT

AAAAGGACGCTCGTTGACCGCGGCTGGGGCAACGGCTGCGGCCTGTTTGGAAAAGGCTCC

CTGGTCACATGCGCGAAGTTTGCATGTTCGAAGAAGATGACGGGCAAAAGCATCCAACCA

GAGAATCTGGAATACCGGATCATGTTGTCCGTGCACGGCAGCCAGCATAGTGGCATGATT

GTGAACGACACCGGTCACGAAACCGACGAGAACCGCGCTAAAGTTGAGATCACCCCGAAC

AGTCCCCGGGCCGAGGCCACGCTGGGAGGCTTCGGATCGCTGGGTCTGGATTGCGAACCC

CGCACCGGACTGGATTTCTCGGATCTCTACTACCTGACGATGAACAATAAGCACTGGCTG

GTGCACAAAGAGTGGTTCCATGATATCCCATTGCCCTGGCATGCCGGTGCCGATACCGGA

ACACCCCACTGGAACAATAAGGAGGCCCTGGTCGAGTTTAAGGACGCGCACGCTAAGCGT

CAAACGGTGGTGGTGCTGGGATCCCAAGAGGGCGCCGTGCACACGGCCCTGGCCGGCGCG

CTGGAGGCCGAGATGGACGGTGCCAAGGGACGCTTGAGCTCCGGACACCTGAAATGCCGC

CTCAAGATGGACAAGCTGCGTCTGAAAGGAGTGTCCTACTCCCTCTGCACCGCCGCGTTC

ACCTTCACTAAGATTCCCGCCGAGACTTTGCACGGTACAGTGACCGTTGAGGTGCAGTAT

GCCGGAACCGATGGCCCTTGCAAAGTCCCGGCCCAAATGGCGGTGGATATGCAGACGCTG

ACGCCTGTGGGCCGGCTCATTACCGCAAACCCAGTCATCACGGAGAGTACCGAGAACTCG

AAGATGATGCTGGAGTTGGACCCCCCGTTTGGCGACAGTTACATCGTGATCGGAGTGGGC

GAAAAGAAGATTACGCACCATTGGCACCGTAGCGGC*AGCACCATCGGCAAGGCCTTCGAG*

*GCCACCGTGCGCGGCGCCAAGCGCATGGCCGTGCTGGGCGACACCGCCTGGGACTTCGGC*

*TCCGTGGGCGGC*

Codon optimized nucleotide sequence for Zika prM-E-436 with
synthetic E secretion signal (Product = ZIKFP-OpE-436-CoOp)
                                                    SEQ ID NO: 4
GCAGAAGTGACCCGCCGCGGCAGCGCATACTATATGTACCTCGATCGTAACGACGCGGGC

GAAGCTATCTCCTTCCCGACCACGCTGGGCATGAACAAGTGCTATATTCAGATTATGGAC

CTGGGCCATATGTGCGACGCGACCATGTCCTACGAATGTCCGATGCTGGACGAAGGAGTT

GAGCCTGATGACGTCGATTGCTGGTGCAATACCACTTCCACCTGGGTGGTGTACGGTACT

TGCCATCACAAAAAGGGCGAAGCCCGCCGTTCCCGTCGCGCTGTCACTCTGCCAAGCCAC

AGCACACGCAAATTGCAGACGAGGAGTCAGACGTGGTTGGAGTCGCGCGAGTACACAAAG

CACCTGATTCGGGTGGAAAATTGGATCTTCCGGAATCCGGGCTTTGCTTTGGCGGCAGCC

GCTATTGCGTGGCTGCTCGGCAGTAGCACGTCG***ATGCGCACCATCATTGCCCTGCTCTTG***

***CTGCTCGTGAGCGGTGCCCACGCC*AGCCGTTGCGTG**GGCGTCAGCAACCGCGATTTCGTG

GAGGGCATGAGCGGTGGAACCTGGGTCGACGTTGTGCTGGAACATGGCGGCTGCGTCACA

GTGATGGCTCAGGACAAGCCGACCGTGGACATCGAGTTGGTTACCACGACGGTTTCCAAC

ATGGCGGAGGTTCGCAGCTACTGCTACGAAGCCAGCATCAGCGATATGGCATCGGACAGC

CGGTGCCCGACCCAGGGAGAAGCATATCTCGACAAGCAGTCCGACACGCAATATGTCTGT

AAAAGGACGCTCGTTGACCGCGGCTGGGGCAACGGCTGCGGCCTGTTTGGAAAAGGCTCC

CTGGTCACATGCGCGAAGTTTGCATGTTCGAAGAAGATGACGGGCAAAAGCATCCAACCA

GAGAATCTGGAATACCGGATCATGTTGTCCGTGCACGGCAGCCAGCATAGTGGCATGATT
```

-continued

GTGAACGACACCGGTCACGAAACCGACGAGAACCGCGCTAAAGTTGAGATCACCCCGAAC

AGTCCCCGGGCCGAGGCCACGCTGGGAGGCTTCGGATCGCTGGGTCTGGATTGCGAACCC

CGCACCGGACTGGATTTCTCGGATCTCTACTACCTGACGATGAACAATAAGCACTGGCTG

GTGCACAAAGAGTGGTTCCATGATATCCCATTGCCCTGGCATGCCGGTGCCGATACCGGA

ACACCCCACTGGAACAATAAGGAGGCCCTGGTCGAGTTTAAGGACGCGCACGCTAAGCGT

CAAACGGTGGTGGTGCTGGGATCCCAAGAGGGCGCCGTGCACACGGCCCTGGCCGGCGCG

CTGGAGGCCGAGATGGACGGTGCCAAGGGACGCTTGAGCTCCGGACACCTGAAATGCCGC

CTCAAGATGGACAAGCTGCGTCTGAAAGGAGTGTCCTACTCCCTCTGCACCGCCGCGTTC

ACCTTCACTAAGATTCCCGCCGAGACTTTGCACGGTACAGTGACCGTTGAGGTGCAGTAT

GCCGGAACCGATGGCCCTTGCAAAGTCCCGGCCCAAATGGCGGTGGATATGCAGACGCTG

ACGCCTGTGGGCCGGCTCATTACCGCAAACCCAGTCATCACGGAGAGTACCGAGAACTCG

AAGATGATGCTGGAGTTGGACCCCCCGTTTGGCGACAGTTACATCGTGATCGGAGTGGGC

GAAAAGAAGATTACGCACCATTGGCACCGTAGCGGC*AGCACCATCGGCAAGGCCTTCGAG*

*GCCACCGTGCGCGGCGCCAAGCGCATGGCCGTGCTGGGCGACACCGCCTGGGACTTCGGC*

*TCCGTGGGCGGC*

French Polynesia prM-E nucleotide sequence (Product = ZIKFP-80E-WT)

SEQ ID NO: 5

GCGGAGGUCACUAGACGUGGGAGUGCAUACUAUAUGUACUUGGACAGAAACGACGCUGGG 60

GAGGCCAUAUCUUUUCCAACCACAUUGGGGAUGAAUAAGUGUUAUAUACAGAUCAUGGAU 120

CUUGGACACAUGUGUGAUGCCACCAUGAGCUAUGAAUGCCCUAUGCUGGAUGAGGGGGUG 180

GAACCAGAUGACGUCGAUUGUUGGUGCAACACGACGUCAACUUGGGUUGUGUACGGAACC 240

UGCCAUCACAAAAAAGGUGAAGCACGGAGAUCUAGAAGAGCUGUGACGCUCCCCUCCCAU 300

UCCACUAGGAAGCUGCAAACGCGGUCGCAAACCUGGUUGGAAUCAAGAGAAUACACAAAG 360

CACUUGAUUAGAGUCGAAAAUUGGAUAUUCAGGAACCCUGGCUUCGCGUUAGCAGCAGCU 420

GCCAUCGCUUGGCUUUUGGGAAGCUCAACGAGCCAAAAAGUCAUAUACUUGGUCAUGAUA 480

CUGCUGAUUGCCCCGGCAUACAGC<u>AUC</u>AGGUGCAUAGGAGUCAGCAAUAGGGACUUUGUG 540

GAAGGUAUGUCAGGUGGGACUUGGGUUGAUGUUGUCUUGGAACAUGGAGGUUGUGUCACC 600

GUAAUGGCACAGGACAAACCGACUGUCGACAUAGAGCUGGUUACAACAACAGUCAGCAAC 660

AUGGCGGAGGUAAGAUCCUACUGCUAUGAGGCAUCAAUAUCGGACAUGGCUUCGGACAGC 720

CGCUGCCCAACACAAGGUGAAGCCUACCUUGACAAGCAAUCAGACACUCAAUAUGUCUGC 780

AAAAGAACGUUAGUGGACAGAGGCUGGGGAAAUGGAUGUGGACUUUUUGGCAAAGGGAGC 840

CUGGUGACAUGCGCUAAGUUUGCAUGCUCCAAGAAAAUGACCGGGAAGAGCAUCCAGCCA 900

GAGAAUCUGGAGUACCGGAUAAUGCUGUCAGUUCAUGGCUCCCAGCACAGUGGGAUGAUC 960

GUUAAUGACACAGGACAUGAAACUGAUGAGAAUAGAGCGAAGGUUGAGAUAACGCCCAAU 1020

UCACCAAGAGCCGAAGCCACCCUGGGGGGUUUUGGAAGCCUAGGACUUGAUUGUGAACCG 1080

AGGACAGGCCUUGACUUUUCAGAUUUGUAUUACUUGACUAUGAAUAACAAGCACUGGUUG 1140

GUUCACAAGGAGUGGUUCCACGACAUUCCAUUACCUUGGCACGCUGGGGCAGACACCGGA 1200

ACUCCACACUGGAACAACAAAGAAGCACUGGUAGAGUUCAAGGACGCACAUGCCAAAAGG 1260

CAAACUGUCGUGGUUCUAGGGAGUCAAGAAGGAGCAGUUCACACGGCCCUUGCUGGAGCU 1320

CUGGAGGCUGAGAUGGAUGGUGCAAAGGGAAGGCUGUCCUCUGGCCACUUGAAAUGUCGC 1380

CUGAAAAUGGAUAAACUUAGAUUGAAGGGCGUGUCAUACUCCUUGUGUACCGCAGCGUUC 1440

ACAUUCACCAAGAUCCCGGCUGAAACACUGCACGGGACAGUCACAGUGGAGGUACAGUAC 1500

```
GCAGGGACAGAUGGACCUUGCAAGGUUCCAGCUCAGAUGGCGGUGGACAUGCAAACUCUG    1560

ACCCCAGUUGGGAGGUUGAUAACCGCUAACCCCGUAAUCACUGAAAGCACUGAGAACUCU    1620

AAGAUGAUGCUGGAACUUGAUCCACCAUUUGGGGACUCUUACAUUGUCAUAGGAGUCGGG    1680

GAGAAGAAGAUCACCCACCACUGGCACAGGAGUGGCAGCACCAUUGGAAAAGCAUUUGAA    1740

GCCACUGUGAGAGGUGCCAAGAGAAUGGCAGUCUUGGGAGACACAGCCUGGGACUUUGGA    1800

UCAGUUGGAGGCGCUCUCAACUCAUUGGGCAAGGGCAUCCAUCAAAUUUUUGGAGCAGCU    1860

UUCAAAUCAUUGUUUGGAGGAAUGUCCUGGUUCUCACAAAUUCUCAUUGGAACGUUGCUG    1940

AUGUGGUUGGGUCUGAACACAAAGAAUGGAUCUAUUUCCCUUAUGUGCUUGGCCUUAGGG    2000

GGAGUGUUGAUCUUCUUAUCCACAGCUGUCUCUGCUG                          2017
```

French Polynesia prM-E amino acid sequence
SEQ ID NO: 6

A E V T R R G S A Y Y M Y L D R N D A G 20
E A I S F P T T L G M N K C Y I Q I M D 40
L G H M C D A T M S Y E C P M L D E G V 60
E P D D V D C W C N T T S T W V V Y G T 80
C H H K K G E A R R S R R A V T L P S H 100
S T R K L Q T R S Q T W L E S R E Y T K 120
H L I R V E N W I F R N P G F A L A A A 140
A I A W L L G S S T S Q K V I Y L V M I 160
L L I A P A Y S I R C I G V S N R D F V 180
E G M S G G T W V D V V L E H G G C V T 200
V M A Q D K P T V D I E L V T T T V S N 220
M A E V R S Y C Y E A S I S D M A S D S 240
R C P T Q G E A Y L D K Q S D T Q Y V C 260
K R T L V D R G W G N G C G L F G K G S 280
L V T C A K F A C S K K M T G K S I Q P 300
E N L E Y R I M L S V H G S Q H S G M I 320
V N D T G H E T D E N R A K V E I T P N 340
S P R A E A T L G G F G S L G L D C E P 360
R T G L D F S D L Y Y L T M N N K H W L 380
V H K E W F H D I P L P W H A G A D T G 400
T P H W N N K E A L V E F K D A H A K R 420
Q T V V V L G S Q E G A V H T A L A G A 440
L E A E M D G A K G R L S S G H L K C R 460
L K M D K L R L K G V S Y S L C T A A F 480
T F T K I P A E T L H G T V T V E V Q Y 500
A G T D G P C K V P A Q M A V D M Q T L 520
T P V G R L I T A N P V I T E S T E N S 540
K M M L E L D P P F G D S Y I V I G V G 560
E K K I T H H W H R S G S T I G K A F E 580
A T V R G A K R M A V L G D T A W D F G 600
S V G G A L N S L G K G I H Q I F G A A 620
F K S L F G G M S W F S Q I L I G T L L 640
M W L G L N T K N G S I S L M C L A L G 660
G V L I F L S T A V S A 672 pHH202 expression vector cassette sequence

SEQ ID NO: 7

GGTACCGTTGCAGGACAGGATGTGGTGCCCGATGTGACTAGCTCTTTGCTGCAGGCCGTCCTA

TCCTCTGGTTCCGATAAGAGACCCAGAACTCCGGCCCCCCACCGCCCACCGCCACCCCCATAC

ATATGTGGTACGCAAGTAAGAGTGCCTGCGCATGCCCCATGTGCCCCACCAAGAGTTTTGCAT

CCCATACAAGTCCCCAAAGTGGAGAACCGAACCAATTCTTCGCGGGCAGAACAAAAGCTTCTG

CACACGTCTCCACTCGAATTTGGAGCCGGCCGGCGTGTGCAAAAGAGGTGAATCGAACGAAAG

ACCCGTGTGTAAAGCCGCGTTTCCAAAATGTATAAAACCGAGAGCATCTGGCCAATGTGCATC

AGTTGTGGTCAGCAGCAAAATCAAGTGAATCATCTCAGTGCAACTAAAGGGGGaATCTAGAaa caacATGAAGACCATTATCGCCCTGTCGTACATCTTTTGCCTGGTGTTCgctagcTCTAGcta gAggctcgagGCCCTTCGAAggatccAGACATGATAAGATACATTGATGAGTTTGGACAAACC

ACAACTAGAATGCAGTGAAAAAAATGCTTTATTTGTGAAATTTGTGATGCTATTGCTTTATTT

GTAACCATTATAAGCTGCAATAAACAAGTTAACAACAACAATTGCATTCATTTTATGTTTCAG

GTTCAGGGGGAGGTGTGGGAGGTTTTTTAAAG

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

I claim:

1. An expression vector comprising a DNA sequence encoding Zika virus pre-membrane and envelope protein, wherein expression of the DNA sequence results in secretion of a soluble envelope protein in the culture medium, wherein the DNA sequence comprises SEQ ID NO:1.

2. An expression vector comprising:
   a DNA sequence encoding Zika virus pre-membrane and envelope protein, wherein expression of the DNA sequence results in secretion of a soluble envelope protein in the culture medium, and
   an expression cassette that comprises SEQ ID NO:7.

3. An expression vector for expression and secretion of heterologous proteins in cultured insect cells, wherein the expression vector comprises the expression cassette shown in SEQ ID NO:7.

4. A method of expressing the expression vector of claim 1 in a cell comprising contacting the cell with the expression vector, wherein the cell is a *Drosophila* cell.

5. A method of expressing the expression vector of claim 1 in a cell comprising contacting the cell with the expression vector, wherein the cell is a *Drosophila melanogaster* Schneider 2 (S2) cell.

6. A method of expressing the expression vector of claim 2 in a cell comprising contacting the cell with the expression vector, wherein the cell is a *Drosophila* cell.

7. A method of expressing the expression vector of claim 2 in a cell comprising contacting the cell with the expression vector, wherein the cell is a *Drosophila melanogaster* Schneider 2 (S2) cell.

* * * * *